United States Patent
Danley

(10) Patent No.: US 6,428,203 B1
(45) Date of Patent: Aug. 6, 2002

(54) POWER COMPENSATION DIFFERENTIAL SCANNING CALORIMETER

(75) Inventor: Robert L. Danley, Collingswood, NJ (US)

(73) Assignee: Ta Instruments, Inc., New Castle, DE (US)

( * ) Notice: Subject to any disclaimer, the term of this patent is extended or adjusted under 35 U.S.C. 154(b) by 55 days.

(21) Appl. No.: 09/643,869

(22) Filed: Aug. 23, 2000

Related U.S. Application Data

(63) Continuation-in-part of application No. 09/533,949, filed on Mar. 23, 2000, now abandoned.

(51) Int. Cl.$^7$ .............................. G01N 1/00; G01K 1/20; G01K 17/04; G01K 17/08
(52) U.S. Cl. .............................. 374/10; 374/1; 374/32; 374/33
(58) Field of Search .......................... 374/10–11, 29–31, 374/33–43, 32

(56) References Cited

U.S. PATENT DOCUMENTS

| | | |
|---|---|---|
| 3,263,484 A | 8/1966 | Watson et al. |
| 3,732,722 A | 5/1973 | Norem et al. |
| 4,095,453 A | 6/1978 | Woo |
| 4,330,933 A | 5/1982 | Bullinger et al. |
| 4,350,466 A | 9/1982 | Bahr et al. |
| 4,530,608 A | 7/1985 | O'Neill |
| 4,614,721 A | 9/1986 | Goldberg ................... 436/147 |
| 4,783,174 A | 11/1988 | Gmelin et al. |
| 5,033,866 A | 7/1991 | Kehl et al. |
| 5,224,775 A | 7/1993 | Reading et al. |
| 5,288,147 A | 2/1994 | Schaefer et al. |
| 5,346,306 A * | 9/1994 | Reading et al. ............... 374/10 |
| 5,474,385 A * | 12/1995 | Reading ....................... 374/11 |
| 5,599,104 A * | 2/1997 | Nakamura et al. ............ 374/12 |
| 5,813,763 A * | 9/1998 | Plotnikov et al. ............. 374/11 |
| 5,842,788 A * | 12/1998 | Danley et al. ................ 374/12 |
| 6,079,873 A * | 6/2000 | Cavicchi et al. .............. 374/10 |
| 6,146,012 A * | 11/2000 | Nakamura et al. ............ 374/10 |
| 6,170,984 B1 * | 1/2001 | Schawe et al. ............... 374/10 |
| 6,200,022 B1 * | 3/2001 | Hammiche et al. ........... 374/46 |

FOREIGN PATENT DOCUMENTS

| | | | | |
|---|---|---|---|---|
| DE | 30 49 105 A | 7/1982 | .......... | G01N/25/20 |
| EP | 0 701 122 | 3/1996 | .......... | G01N/25/48 |
| JP | 02082145 | * | 3/1990 | |

OTHER PUBLICATIONS

"A Differential Scanning Calorimeter for Quantitative Differntial Thermal Analysis", E..S. Watson and M.J. O'Neill, Analytical Chemistry vol. 36, No. 7, pp. 1233–1238 (Jun. 1994).

"The Analysis of Temperature Controlled Scanning Calorimeter", M.J. O'Neill, Analytical Chemistry vol. 36, No. 7, pp. 1238–1245 (Jun. 1964).

"Differential Scanning Calorimetry an Introduction for Practioners", G. Hohne, W. Hemminger, and H.J. Flammersheim (Springer–Verlag 1996).

* cited by examiner

Primary Examiner—Diego Gutierrez
Assistant Examiner—Gail Verbitsky
(74) Attorney, Agent, or Firm—Shaw Pittman LLP

(57) ABSTRACT

A power compensation differential scanning calorimeter that uses one absolute temperature measurement, two differential temperature measurements, a differential power measurement, and a five-term heat flow equation to measure the sample heat flow. The calorimeter is calibrated by running two sequential calibration experiments. In a preferred embodiment, the first calibration experiment uses empty sample and reference pans, and the second calibration experiment uses sapphire specimens in the sample and reference holders. In an alternate embodiment, sapphire calibration specimens are used in both the first and second calibration experiments.

66 Claims, 5 Drawing Sheets

POWER COMPENSATION DIFFERENTIAL SCANNING CALORIMETER

The present application is a continuation-in-part application of U.S. patent application Ser. No. 09/533,949, filed Mar. 23, 2000, now abandoned, which is incorporated herein by reference. The present application also incorporates by reference U.S. patent application Ser. No. 09/643,870, entitled "Heat Flux Differential Scanning Calorimeter", filed Aug. 23, 2000, listing Robert L. Danley as the inventor.

BACKGROUND

1. Field of the Invention

The present invention relates to a thermal analysis instrument, and more particularly, to a power compensation differential scanning calorimeter.

2. Background of the Invention

Differential scanning calorimeters (DSCs) measure the flow of heat to a sample to be analyzed as a function of time and temperature. DSCs are described in "Differential Scanning Calorimetry: an Introduction for Practitioners," G. H öhne, W. Hemminger and H. J. Flammersheim (Springer-Verlag: 1996) and "Thermal Analysis," Bernhard Wunderlich (Academic Press, 1990).

Power compensation DSCs are a specific type of DSC that measure the difference in power supplied to the sample compared to the reference throughout the analysis. Power compensation DSCs are described in "A Differential Scanning Calorimeter for Quantitative Differential Thermal Analysis", E. S. Watson and M. J. O'Neill, Analytical Chemistry Vol. 36, No 7, pp. 1233–1238 (June 1964), "The Analysis of a Temperature-Controlled Scanning Calorimeter", M. J. O'Neill, Analytical Chemistry Vol. 36, No 7, pp. 1238–1245 (June 1964), and in U.S. Pat. No. 3,263,484 to Watson and O'Neill and U.S. Pat. No. 3,732,722 to Norem, O'Neill, and Richmond, which are incorporated by reference herein.

A sample to be analyzed and a reference are heated (or cooled) in two independent sample holders. Each of the sample holders incorporates a detector to measure the temperature of the sample holder and a heating element to heat the sample holder. The sample holders are heated (or cooled) so that the average temperature of the sample holders follows the desired temperature program. Because of the presence of a sample, the temperature of the two sample holders should diverge as the average temperature of the sample holders is increased (or decreased). Typically, the sample would heat (or cool) more slowly and the reference would heat (or cool) more rapidly than the programmed heating (or cooling) rate. To prevent this from occurring, a proportional controller regulates the power supplied to the sample holder and to the reference holder. The power supplied to the sample holder is increased (or decreased) by a small amount and the power supplied to the reference is decreased (or increased) by the same amount so that the temperature difference between the sample and reference is controlled. This small differential power is approximately equal to the heat flow to the sample and is the measured heat flow.

FIG. 1 shows a thermal network model that may be used to represent certain configurations of power compensation DSCs. $T_0$ is the temperature of the isothermal enclosure surrounding the sample holders, $T_s$ is the temperature of the sample holder and $T_r$ is the temperature of the reference holder. $R_s$ and $R_r$ represent the thermal resistance of the sample and reference portions of the calorimeter, respectively. $C_s$ and $C_r$ represent the thermal capacitance of the sample and reference portions of the calorimeter, respectively. Thermal capacitance is the product of mass and specific heat and is a measure of the heat storage capacity of a body. The heat flow to the sample and the heat flow to the reference and their pans are represented by $q_s$ and $q_r$, respectively. The power supplied to the sample and the power supplied to the reference holders are represented by $p_s$ and $p_r$, respectively. During the execution of a thermal program the temperature of the isothermal enclosure $T_0$ is constant. Sample and reference powers $p_s$ and $p_r$ are applied to the sample and reference holders to maintain the average heating rate and to control the difference in temperature between the sample and reference holders. Performing a heat balance on the sample holder yields:

$$q_s = \frac{T_o - T_s}{R_s} + p_s - C_s \cdot \frac{dT_s}{d\tau} \tag{1}$$

Similarly, a heat balance on the reference holder gives, $$q_r = \frac{T_o - T_r}{R_r} + p_r - C_r \cdot \frac{dT_r}{d\tau} \tag{2}$$

The desired quantity is the difference between the sample and reference heat flows:

$$q = q_s - q_r \tag{3}$$

Substituting for $q_s$ and $q_r$ yields:

$$q = p_s - p_r + \frac{T_o - T_s}{R_s} - \frac{T_o - T_r}{R_r} - C_s \cdot \frac{dT_s}{d\tau} + C_r \cdot \frac{dT_r}{d\tau} \tag{4}$$

Substitute the following expressions into the heat flow equation:

$$\Delta T = T_s - T_r, \Delta T_0 = T_0 - T_s, \Delta p_s = p_s - p_r \tag{5}$$

The result is the power compensation DSC heat flow equation:

$$q = \Delta p + \Delta T_o \cdot \left( \frac{R_r - R_s}{R_r \cdot R_s} \right) - \frac{\Delta T}{R_r} + (C_r - C_s) \cdot \frac{dT_s}{d\tau} - C_r \cdot \frac{d\Delta T}{d\tau} \tag{6}$$

This equation has five terms. The first term is the difference in power supplied to the sample position versus the power supplied to the reference position. The second term accounts for differences between the thermal resistances of the sample and reference holders. The third term accounts for the heat flow that results from the difference in temperature between the sample and reference. The fourth term is the heat flow resulting from imbalances in thermal capacitance between the sample and reference holders. The fifth term reflects heat flow resulting from differences in heating rate between the sample and reference holders. In the prior art, this equation is not used; instead a very simplified equation is used:

$$q = K \cdot \Delta T \tag{7}$$

where K is a temperature dependent proportionality factor. This equation does not include the effects of imbalances between the sample and reference holders (the second and fourth terms in the heat flow equation), nor does it include the fifth term which expresses the differences in heating rate between the sample and reference holders. In essence, in the prior art it is assumed that the DSC is perfectly balanced, i.e., that $R_s=R_r$ and that $C_s=C_r$. In reality, because of manufacturing imprecision and the variability of the heat exchange processes between the sample holder and the isothermal enclosure and between the reference holder and the isothermal enclosure, imbalances generally exist. These imbalances contribute to baseline heat flow deviations that may be significant.

The fifth term is generally very nearly equal to zero, except when a transition is occurring in the sample, for instance during a melt. Usually the transition heat flow signal is integrated over a suitable baseline to obtain the total energy of the transition. Because the integral of the fifth term over the transition is zero, it is conventionally ignored in the prior art. However, it may contribute significantly to the shape of the heat flow curve during a transition. Thus, by including the fifth term, the dynamic response of the instrument is improved. Also, as noted by Höhne et. al., referenced above, this term must be taken into account when a partial integration of the transition peak is performed (for instance when kinetic investigations to determine purity are undertaken). When the fifth term is included, the return to baseline after the completion of a transition is more rapid. Because the resolution of a DSC is its ability to separate transitions that occur in a sample within a small temperature interval, and that ability is determined solely by how quickly the heat flow signal decays after a transition is complete, including the fifth term of the DSC heat flow equation improves the resolution of the DSC by increasing the rate of decay of the heat flow signal after a transition is completed.

SUMMARY OF THE INVENTION

The present invention is a power compensation differential scanning calorimeter that uses two differential temperature measurements and a five term heat flow equation to model the instrument. The present invention is also a method by which the thermal parameters required to apply the five term heat flow equation are determined. Differential scanning calorimeters employing this invention will have empty DSC cell heat flow that is much closer to zero (leading to improved baselines) and will have substantially improved resolution over conventional instruments.

In a preferred embodiment, the two differential temperature measurements are the differential temperature $\Delta T_0$ across thermal resistance $R_s$, and the differential temperature $\Delta T$ between the sample and reference holders. The absolute temperature of the sample holder and the power difference between the sample and reference holders are also measured (i.e., the differential power to the sample with respect to the reference). Additionally, the four thermal parameters, $R_s$, $R_r$, $C_s$ and $C_r$ must be known. The use of two differential temperature measurements allows the use of a heat flow model that includes all five terms of the five term heat flow equation. The heat flow signal that results has improved baseline performance and improved dynamic response. In particular, because the heat flow signal is much greater during a melt, the calorimeter has greater sensitivity during the melt.

Other choices of the two differential temperature measurements are also suitable, as explained below.

The present invention also comprises a method by which the four thermal parameters $C_s$, $C_r$, $R_s$, $R_r$ are determined. This determination constitutes heat flow calibration of the DSC.

Heat flow calibration requires two experiments from which the four thermal parameters can be calculated. The first experiment is performed with an empty DSC cell. The DSC program begins with an isothermal temperature segment at a temperature below the lowest temperature of the desired calibration range, followed by a constant heating rate temperature ramp, and ending with an isothermal temperature segment above the highest temperature of the desired calibration range. The heating rate should be the same as the heating rate that is to be used for subsequent experiments. The second calibration experiment is performed with sapphire samples loaded in both the sample and reference holders. The same thermal program is used for the second experiment as was used for the first (empty DSC) experiment. The two calibration experiments and the calculation of the thermal parameters based on the experiments are explained in detail below.

OBJECTS OF THE INVENTION

It is the object of the present invention to provide a power compensation DSC that uses two differential temperature measurements, one absolute temperature measurement and a differential power measurement, so that a five term heat flow equation may be used to calculate a more complete and correct measure of the heat flow to the sample.

Another object of the present invention is to disclose a method by which the detector parameters needed to employ the five term heat flow equation may be determined.

A further object of the present invention is to provide a power compensation DSC with improved baseline heat flow and improved dynamic response.

DETAILED DESCRIPTION OF A PREFERRED EMBODIMENT OF THE INVENTION

Figure 2:
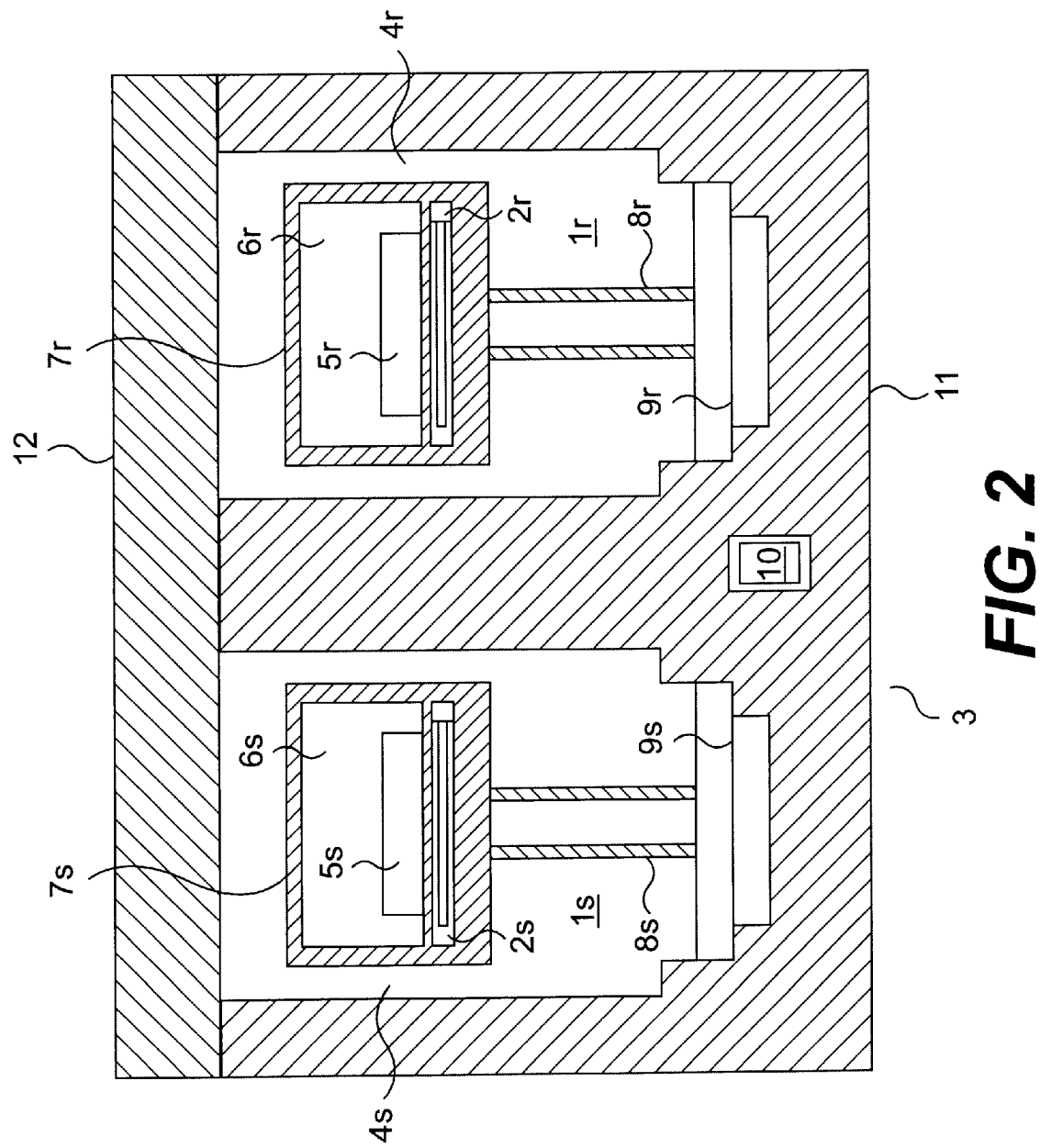
FIG. 2 is a schematic diagram of the power compensation DSC of the present invention.

FIG. 2 is a schematic diagram of a cross-sectional view of a power compensation DSC cell of the present invention. The DSC cell comprises a sample holder assembly is and a reference holder assembly 1r installed in an isothermal enclosure 3. Overall, the sample and reference holder assemblies are manufactured to be as identical as possible. Sample holder 1s has a body 4s in which are embedded a temperature detector 2s, and a heating element (not shown in FIG. 2). A sample in a sample pan 5s is inserted in the cavity 6s of the sample holder, which is closed by a lid 7s. The body of the sample holder 4s is supported by thermal resistor 8s, which is attached to flange 9s. The thermal resistor is the principal path for heat exchange between the sample holder and the isothermal enclosure and allows the sample holder to be heated to temperatures much higher than the isothermal enclosure by applying a modest quantity of heater power. Thermal resistor 8s is a tubular member with a small cross-sectional area in the direction normal to heat flow, as compared with its length in the direction of heat flow.

Similarly, reference holder 1r has a body 4r in which are embedded a temperature detector 2r, and a heating element (not shown in FIG. 2). Reference pan 5r is inserted in the cavity 6r of reference holder 1r, which is closed by lid 7r. The body of the reference holder 4r is supported by thermal resistor 8r, which is attached to flange 9r. The thermal resistor is the principal path for heat exchange between the reference holder 1r and the isothermal enclosure, and allows the reference holder to be heated to temperatures much higher than the isothermal enclosure by modest heater power. It is a tubular member with a small cross-sectional area in the direction normal to heat flow as compared with its length in the direction of heat flow. A reference material could be placed in a reference pan 5r, which is inserted in the cavity of reference holder 1r, although the usual practice is to omit the reference material and place an empty pan 5r in reference holder 1r.

The isothermal enclosure 3 comprises a body 11 and a removable lid 12 that allows access to the sample and reference holders for loading the sample and reference. Flange 9s of the sample holder is joined to the body 11 of the isothermal enclosure so that heat flows from the sample holder and sample through the thermal resistor 8s to the isothermal body. Isothermal enclosure temperature detector 10 is installed in the body 11 of the isothermal enclosure 3 to measure the isothermal temperature; the difference between this temperature and the temperature of the sample holder is $\Delta T_0$. The isothermal body is cooled by various means, for example a liquid cryogen, mechanical refrigeration, water or air. The isothermal enclosure is constructed of a high thermal conductivity material, typically aluminum, to minimize variation of temperature within the enclosure.

This embodiment of the present invention uses the sample temperature measurement as the only absolute temperature measurement. It also measures the differential temperature between the sample and reference holders, the differential temperature between the sample holder and the isothermal enclosure, and the differential power to the sample with respect to the reference. The differential power to the sample with respect to the reference is measured, for example, by measuring the power to the sample holder and the power to the reference holder separately, and obtaining the difference between the separate measurements. The power to the sample holder and the power to the reference holder can be measured in a number of different ways, for example by instrumentation that measures the voltages and currents to the sample and reference heaters. Thus, this embodiment uses a combination of a single absolute temperature measurement (the sample temperature), two differential temperature measurements (sample/reference and sample/enclosure) and a differential power measurement (sample/reference) to obtain the quantities needed to calculate the differential heat flow to the sample according to the power compensation DSC heat flow equation (equation 6, reproduced here for convenience):

$$q = \Delta p + \Delta T_o \cdot \left(\frac{R_r - R_s}{R_r \cdot R_s}\right) - \frac{\Delta T}{R_r} + (C_r - C_s) \cdot \frac{dT_s}{d\tau} - C_r \cdot \frac{d\Delta T}{d\tau} \quad (6)$$

It will be recognized that other combinations of a single absolute temperature and two differential temperature measurements may also be used with a five term heat flow equation. The improvements of the current invention can also be obtained using the other configurations. There are three possible choices for the single absolute temperature measurement: the sample holder temperature, the reference holder temperature and the isothermal enclosure temperature. Each of these can be used with any two of the three possible differential temperature measurements to achieve the same results. Thus the sample temperature $T_s$ can be used as the absolute temperature measurement with differential temperature measurements $T_0-T_s$ and $T_s-T_r$ as in the preferred embodiment, or with $T_0-T_s$ and $T_0-T_r$ or with $T_s-T_r$ and $T_0-T_r$. The reference temperature $T_r$ can be used as the absolute temperature measurement with differential temperature measurements $T_s-T_r$ and $T_0-T_r$ or with $T_s-T_r$ and $T_0-T_s$ or with $T_s-T_r$ and $T_0-T_s$. The base temperature $T_0$ can be used as the absolute temperature measurement with $T_0-T_s$ and $T_s-T_r$, or with $T_0-T_s$ and $T_0-T_r$, or with $T_0-T_r$ and $T_s-T_r$. Thus, there are eight additional configurations that can give the same information if the five term heat flow equation is rewritten accordingly. All nine of the possible configurations are within the scope of the present invention.

Method for Determining Thermal Parameters

To use the five term Power Compensation DSC heat flow equation, the four thermal parameters $C_s$, $C_r$, $R_s$, $R_r$ must be determined. Determination of these parameters constitutes heat flow calibration of the DSC.

Heat flow calibration requires two experiments from which the four thermal parameters can be calculated. The first experiment is performed with an empty DSC cell. The DSC program begins with an isothermal temperature segment at a temperature below the lowest temperature of the desired calibration range, followed by a constant heating rate temperature ramp, and ending with an isothermal temperature segment above the highest temperature of the desired calibration range. The heating rate should be the same that is to be used for subsequent experiments. The second calibration experiment is performed, for example, with sapphire specimens loaded in both the sample and reference holders. Other materials having known thermal properties and no transitions in the temperature range of interest may be used instead of sapphire. The same thermal program is used in the second experiment as was used for the first empty DSC experiment.

Beginning with the heat balance equation for the sample side, the heat flow during the empty DSC experiment is set equal to zero, and the heat balance equation becomes:

$$\frac{\Delta T_{o1}}{R_s} + p_{s1} - C_s \cdot \frac{dT_{s1}}{d\tau} = 0 \quad (8)$$

The numerical subscript 1 indicates the first calibration experiment. For the second calibration experiment using sapphire specimens, the sample heat flow is set equal to:

$$q_{s2} = m_{s2} \cdot C_{sapph} \cdot \frac{dT_{s2}}{d\tau} \quad (9)$$

where $m_{s2}$ is the mass of the sapphire sample, $C_{sapph}$ is the known heat capacity of sapphire and the numerical subscript 2 indicates the second calibration experiment. For the second calibration experiment, the heat balance equation becomes:

$$\frac{\Delta T_{o2}}{R_s} + p_{s2} - C_s \cdot \frac{dT_{s2}}{d\tau} = m_{s2} \cdot C_{sapph} \cdot \frac{dT_{s2}}{d\tau} \qquad (10)$$

Solving these two equations simultaneously for $C_s$ and $R_s$ gives:

$$C_s = \frac{\Delta T_{o1} \cdot \left(m_{s2} \cdot C_{sapph} \cdot \frac{dT_{s2}}{d\tau} - p_{s2}\right) + \Delta T_{o2} \cdot p_{s1}}{\Delta T_{o2} \cdot \frac{dT_{s1}}{d\tau} - \Delta T_{o1} \cdot \frac{dT_{s2}}{d\tau}} \qquad (11)$$

$$R_s = \frac{\Delta T_{o2} \cdot \frac{dT_{s1}}{d\tau} - \Delta T_{o1} \cdot \frac{dT_{s2}}{d\tau}}{\frac{dT_{s1}}{d\tau} \cdot \left(m_{s2} \cdot C_{sapph} \cdot \frac{dT_{s2}}{d\tau} - p_{s2}\right) + \frac{dT_{s2}}{d\tau} \cdot p_{s1}} \qquad (12)$$

Similarly, the heat balance equations for the empty and the sapphire calibration runs on the reference side give:

$$\frac{T_{o1} - T_{r1}}{R_r} + p_{r1} - C_r \cdot \frac{dT_{r1}}{d\tau} = 0 \qquad (13)$$

$$\frac{T_{o2} - T_{r2}}{R_r} + p_{r2} - C_r \cdot \frac{dT_{r2}}{d\tau} = m_{r2} \cdot C_{sapph} \cdot \frac{dT_{r2}}{d\tau} \qquad (14)$$

The reference temperature $T_r$ is not measured directly. Substituting for $T_r$:

$$T_r = T_s - \Delta T \qquad (15)$$

The heat balance equations become:

$$\frac{\Delta T_{o1} + \Delta T_1}{R_r} + p_{r1} - C_r \cdot \left(\frac{dT_{s1}}{d\tau} - \frac{d\Delta T_1}{d\tau}\right) = 0 \qquad (16)$$

$$\frac{\Delta T_{o2} + \Delta T_2}{R_r} + p_{r2} - C_r \cdot \left(\frac{dT_{s2}}{d\tau} - \frac{d\Delta T_2}{d\tau}\right) = m_{r2} \cdot C_{sapph} \cdot \left(\frac{dT_{s2}}{d\tau} - \frac{d\Delta T_2}{d\tau}\right) \qquad (17)$$

Simultaneous solution of these equations gives:

$$C_r = \frac{(\Delta T_{o1} + \Delta T_1) \cdot \left[m_{r2} \cdot C_{sapph} \cdot \left(\frac{dT_{s2}}{d\tau} - \frac{d\Delta T_2}{d\tau}\right) - p_{r2}\right] + (\Delta T_{o2} + \Delta T_2) \cdot p_{r1}}{(\Delta T_{o1} + \Delta T_1) \cdot \left(\frac{d\Delta T_2}{d\tau} - \frac{dT_{s2}}{d\tau}\right) + (\Delta T_{o2} + \Delta T_2) \cdot \left(\frac{dT_{s1}}{d\tau} - \frac{d\Delta T_1}{d\tau}\right)} \qquad (18)$$

$$R_r = \frac{(\Delta T_{o1} + \Delta T_1) \cdot \left(\frac{d\Delta T_2}{d\tau} - \frac{dT_{s2}}{d\tau}\right) + (\Delta T_{o2} + \Delta T_2) \cdot \left(\frac{dT_{s1}}{d\tau} - \frac{d\Delta T_1}{d\tau}\right)}{\left[m_{r2} \cdot C_{sapph} \cdot \left(\frac{dT_{s1}}{d\tau} - \frac{d\Delta T_1}{d\tau}\right) - p_{r2}\right] \cdot \left(\frac{dT_{s1}}{d\tau} - \frac{d\Delta T_1}{d\tau}\right) - p_{r1} \cdot \left(\frac{d\Delta T_2}{d\tau} - \frac{dT_{s2}}{d\tau}\right)} \qquad (19)$$

In an alternate embodiment, both calibration experiments may contain specimens. The specimens in the two calibration experiments must have substantially different masses. For example, the sample (reference) specimen masses are substantially different if the mass of the sample (reference) specimen for the first calibration experiment is twice the mass of the sample (reference) specimen for the second experiment, whereas a 5% difference would not be substantial. In this embodiment, the heat balance equation for the first experiment on the sample side becomes:

$$\frac{\Delta T_{o1}}{R_s} + p_{s1} - C_s \cdot \frac{dT_{s1}}{d\tau} = m_{s1} \cdot C_{sapph} \cdot \frac{dT_{s1}}{d\tau} \qquad (20)$$

and the heat balance equation for the first experiment on the reference side becomes:

$$\frac{\Delta T_{o1} + \Delta T_1}{R_r} + p_{r1} - C_r \cdot \left(\frac{dT_{s1}}{d\tau} - \frac{d\Delta T_1}{d\tau}\right) = m_{r1} \cdot C_{sapph} \cdot \left(\frac{dT_{s1}}{d\tau} - \frac{d\Delta T_1}{d\tau}\right) \qquad (21)$$

Solving simultaneously as before gives:

$$C_s = \frac{\Delta T_{o1} \cdot \left(m_{s2} \cdot C_{sapph} \cdot \frac{dT_{s2}}{d\tau} - p_{s2}\right) + \Delta T_{o2} \cdot \left(p_{s1} - m_{s1} \cdot C_{sapph} \cdot \frac{dT_{s1}}{d\tau}\right)}{\Delta T_{o2} \cdot \frac{dT_{s1}}{d\tau} - \Delta T_{o1} \cdot \frac{dT_{s2}}{d\tau}} \qquad (22)$$

$$R_s = \frac{\Delta T_{o2} \cdot \frac{dT_{s1}}{d\tau} - \Delta T_{o1} \cdot \frac{dT_{s2}}{d\tau}}{\frac{dT_{s1}}{d\tau} \cdot \left(m_{s2} \cdot C_{sapph} \cdot \frac{dT_{s2}}{d\tau} - p_{s2}\right) + \frac{dT_{s2}}{d\tau} \cdot \left(p_{s1} - m_{s1} \cdot C_{sapph} \cdot \frac{dT_{s1}}{d\tau}\right)} \qquad (23)$$

$$C_r = \frac{(\Delta T_{o1} + \Delta T_1) \cdot \left[m_{r2} \cdot C_{sapph} \cdot \left(\frac{dT_{s2}}{d\tau} - \frac{d\Delta T_2}{d\tau}\right) - p_{r2}\right] + (\Delta T_{o2} + \Delta T_2) \cdot \left[p_{r1} - m_{r1} \cdot C_{saph} \cdot \left(\frac{dT_{s1}}{d\tau} - \frac{d\Delta T_1}{d\tau}\right)\right]}{(\Delta T_{o1} + \Delta T_1) \cdot \left(\frac{d\Delta T_2}{d\tau} - \frac{dT_{s2}}{d\tau}\right) + (\Delta T_{o2} + \Delta T_2) \cdot \left(\frac{dT_{s1}}{d\tau} - \frac{d\Delta T_1}{d\tau}\right)} \qquad (24)$$

$$R_r = \frac{(\Delta T_{o1} + \Delta T_1) \cdot \left(\frac{d\Delta T_2}{d\tau} - \frac{dT_{s2}}{d\tau}\right) + (\Delta T_{o2} + \Delta T_2) \cdot \left(\frac{dT_{s1}}{d\tau} - \frac{d\Delta T_1}{d\tau}\right)}{\left(\frac{dT_{s1}}{d\tau} - \frac{d\Delta T_1}{d\tau}\right) \cdot \left[m_{r2} \cdot C_{sapph} \cdot \left(\frac{dT_{s2}}{d\tau} - \frac{d\Delta T_2}{d\tau}\right) - p_{r2}\right] + \left(\frac{dT_{s2}}{d\tau} - \frac{d\Delta T_2}{d\tau}\right) \cdot \left[p_{r1} - m_{r1} \cdot C_{sapph} \cdot \left(\frac{dT_{s1}}{d\tau} - \frac{d\Delta T_1}{d\tau}\right)\right]} \qquad (25)$$

The thermal capacitances and resistances are used to calculate sample heat flow during a DSC experiment. They may be used as tabular data, with suitable interpolation for intermediate values, or they may be fitted by a mathematical expression, e.g., to a polynomial. In either case, the calculated capacitances and resistances must be applied as a function of temperature. Typically, the sapphire specimen masses range from 25 to 75 mg.

The power to the sample $p_s$ and the power to the reference $p_r$ are measured separately during the calibration step. The differential power is obtained by subtracting $p_r$ from $p_s$.

Numerical Simulation

Figure 3:
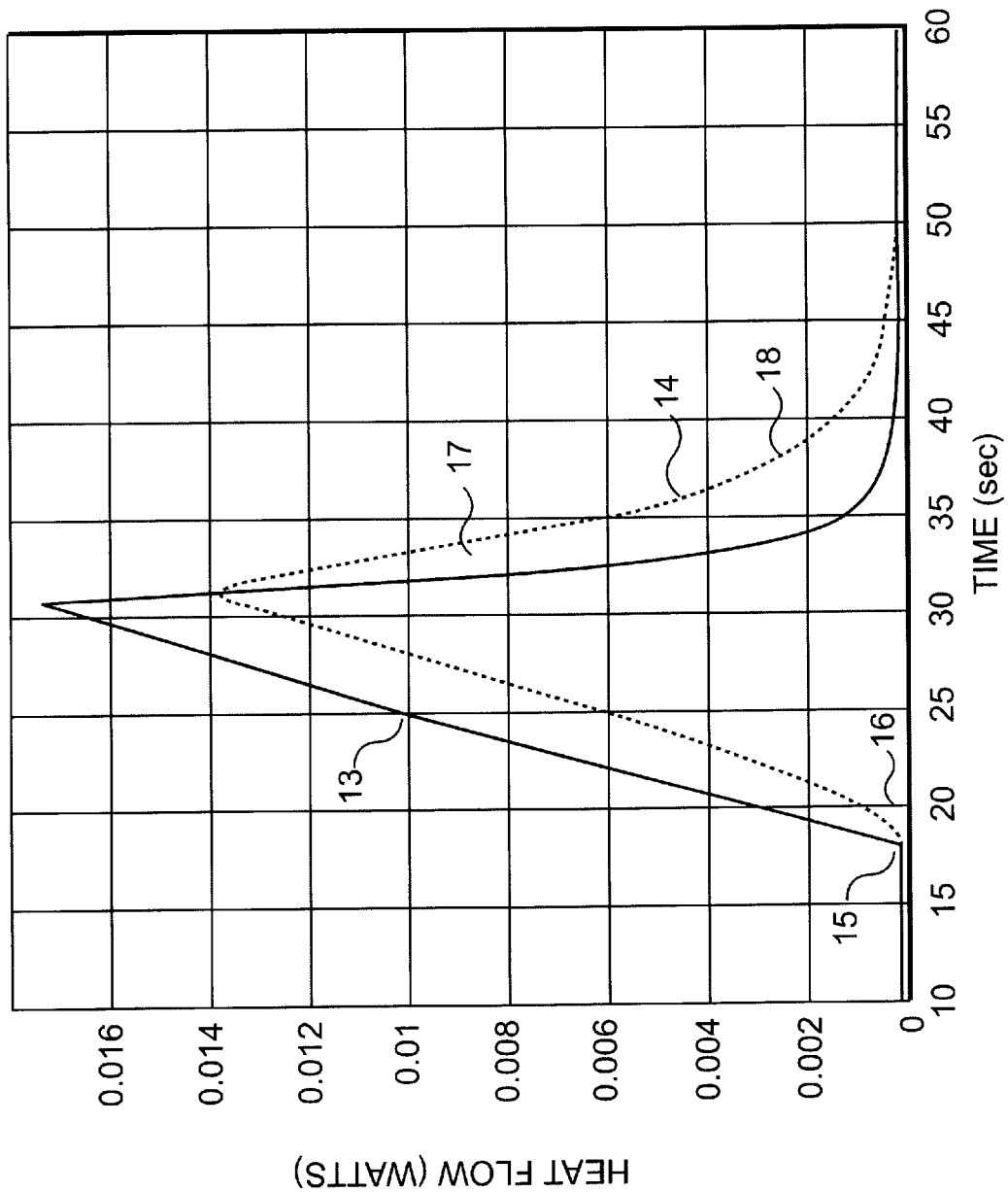
FIG. 3 is a comparison of the heat flow in a power compensation DSC measured according to the present invention (solid line) and according to the prior art (dotted line).

FIG. 3 shows the result of a numerical simulation of a 5 mg indium sample heated at 10° C./min through its melting point in a power compensation DSC. Heat flow is calculated using the five term equation (solid curve, trace 13) and using the conventional single term heat flow equation (dotted curve, trace 14). The melt onset is the point at which the indium sample begins to melt, at which temperature the heat flow to the sample increases abruptly. Ideally, the heat flow curve turns upward discontinuously when melting commences, but because of heat transfer effects within the sample, the sample pan, the detector and the interfaces between them, the heat flow curve is rounded off, or smeared. This smearing reduces the precision with which the temperature of the onset can be determined. The onset temperature is taken as the melting temperature of the sample, which is an important experimental result. Thus, sharper melt onset heat flow curves are preferred. Melt onset 15 of the five term heat flow curve is clearly much sharper than melt onset 16 of the single term heat flow equation. Notice also that the shape of the melt onset is distinctly different for the five term heat flow equation than for the single term equation.

During the melt, the heat flow continues to increase until the sample is entirely melted, at which point the heat flow to the sample decreases abruptly and the heat flow curve decays. If a second transition begins before the heat flow signal has decayed completely, the two transitions are difficult to separate (without introducing additional uncertainties) for purposes of determining the integrated peak areas of the two transitions, and the onset temperature of the second transition is more difficult to determine. Thus, the speed of the decay of the heat flow signal after the completion of the transition is important, with faster decay preferable because it improves the resolution of the calorimeter. The baseline return 17 of the five term heat flow signal is clearly much more rapid than baseline decay 18 of the single term heat flow signal, giving improved resolution. Because the heat flow signal is much greater during a melt, the calorimeter has greater sensitivity during the melt.

In an alternate embodiment, the present invention could be implemented using equation 4 instead of equation 6, by making individual measurements of sample and reference temperatures, and of the power supplied to the sample holder and reference holder, instead of by making differential measurements. The present invention could also be implemented by using a combination of differential and individual measurements.

FURTHER CALCULATION

A further calculation that accounts for the heat flows associated with the sample and reference pans is described below. This is a method for calculating sample heat flow in a Differential Scanning Calorimeter in which the effect of heat storage in the sample pans and the difference in heating rate between sample and reference are included. Accounting for heat flow associated with the pans and the difference between sample and reference heating rate gives a more accurate sample heat flow measurement and improves resolution, which is the ability to separate closely spaced thermal events in the heat flow result.

Differential Scanning Calorimeters measure the heat flow to a sample as the sample temperature is varied in a controlled manner. There are two basic types of DSC, heat flux and power compensation. Brief descriptions of the two types of DSC are included below. For more detailed information on the construction and theory of DSC, see "Differential Scanning Calorimetry an Introduction for Practitioners", G. Höhne, W. Hemminger and H.-J. Flammersheim (Springer-Verlag, 1996).

Heat flux DSCs include a sensor to measure heat flow to a sample to be analyzed. The sensor has a sample position and a reference position. The sensor is installed in an oven whose temperature is varied dynamically according to a desired temperature program. As the oven is heated or cooled, the temperature difference between the sample and reference positions of the sensor is measured. This temperature difference is assumed to be proportional to the heat flow to the sample.

Power compensation DSCs include a sample and a reference holder installed in a constant temperature enclosure. Each of the holders has a heater and a temperature sensor. The average of the sample and reference holder temperatures is used to control temperature, which follows the desired temperature program. In addition, differential power proportional to the temperature difference between the holders is added to the average power to the sample holder and subtracted from the average power to the reference holder in an effort to reduce the temperature difference between sample and reference holders to zero. The differential power is assumed to be proportional to the sample heat flow and is obtained by measuring the temperature difference between the sample and reference holder. In commercial power compensation DSCs, the difference between sample and reference temperature is generally not zero because a proportional controller is used to control the differential power.

A sample to be analyzed is loaded into a pan and placed on the sample position of the DSC. An inert reference material may be loaded into a pan and placed on the reference position of the DSC although usually the reference pan is empty. The temperature program for conventional DSC typically includes combinations of linear temperature ramps and constant temperature segments. Modulated DSC uses a temperature program in which periodic temperature oscillations are superposed on linear ramps and isothermal segments. The experimental result is the sample heat flow versus temperature or time. The heat flow signal is the result of heat flow to or from the sample due to its specific heat and as a result of transitions occurring in the sample.

During the dynamic portion of the DSC experiment, a temperature difference is created between the sample and reference positions of the DSC. In heat flux DSC the temperature difference results from the combination of three differential heat flows. The difference between the sample and reference heat flow, the difference between sample and reference sensor heat flow and the difference between sample and reference pan heat flow. In power compensation DSC the temperature difference results from the combination of three differential heat flows plus the differential power supplied to the sample holders. The differential heat flows are: the difference between the sample and reference heat flow, the difference between sample and reference holder heat flow and the difference between sample and reference pan heat flow. The heat flow difference between the sample and reference consists of heat flow due to the heat capacity difference between the sample and reference, the heat flow of a transition, or the difference in heating rate that occurs during a MDSC experiment. The heat flow difference between the sample and reference sections of the DSC is the result of thermal resistance and capacitance imbalances in the sensor or between the holders and the difference in heating rate that occurs between the sample and reference sections of the DSC during a transition or during a MDSC experiment. Similarly, the heat flow difference between the sample and reference pans is the result of mass differences between the pans and the difference in heating rate that occurs during a sample transition or during an MDSC experiment.

In conventional heat flux DSCs the sensor imbalance and pan imbalance are assumed to be insignificant and the differences in heating rates are ignored. In conventional power compensation DSC the holder imbalance and pan imbalance are assumed to be insignificant and the differences in heating rates are ignored. When the balance assumptions are satisfied and the sample heating rate is the same as the programmed heating rate, the temperature difference is proportional to the sample heat flow and the differential temperature gives an accurate measure of the sample heat flow. The sample heat flow is only proportional to the measured temperature difference between sample and reference when the heating rate of the sample and reference are identical, the sensor is perfectly symmetrical, and the pan masses are identical. Proportionality of sample heat flow to temperature difference for a balanced sensor and pans occurs only during portions of the experiment when the instrument is operating at a constant heating rate, the sample is changing temperature at the same rate as the instrument and there are no transitions occurring in the sample.

During Modulated DSC experiments, the heating rates of the sample and reference are generally not the same and the difference between measured sample and reference temperatures is not proportional to the sample heat flow. Thus, the sample heat flow from a conventional DSC is not the actual sample heat flow, but includes the effects of imbalances and differences in heating rates; in other words the DSC sample heat flow measurement is smeared. For many DSC experiments, the smeared sample heat flow is a sufficiently accurate result. For example, when the desired experimental result is the total energy of the transition, like the heat of fusion of a melt, the total peak area is integrated over a suitable baseline and the result from a conventional DSC is sufficiently accurate. If however, partial integration of the peak area is required (for example in the study of reaction kinetics), the smeared sample heat flow of conventional DSC cannot be used. Another example of when the conventional DSC result is inadequate is when two or more transitions in a sample occur within a small temperature interval. In that case, the transitions may be poorly separated because of the smearing effects. The improvement in resolution obtained by using the present method greatly improves the separation of closely spaced transitions. In any case, the heat flow signal from conventional DSC does not accurately portray the sample heat flow during a transition.

During a transition, the heat flow to the sample increases or decreases from the pre-transition value depending upon whether the transition is exothermic or endothermic and whether the DSC is being heated or cooled. The change in sample heat flow causes the heating rate of the sample to be different from that of the DSC and as a consequence, the sample pan and sensor heating rates become different from the programmed heating rate.

U.S. patent application Ser. No. 09/533,949 (the '949 application), incorporated by reference herein, discloses a heat flux DSC that uses a four term heat flow equation to account for sensor imbalances and differences in heating rate between the sample and reference sections of the sensor. Heat flow results from that invention show improved dynamic response and hence improved resolution along with improvements in the empty DSC cell heat flow. However, the heat flow signal obtained from the practice of that invention still includes the effects of the sample pans.

The present invention, as described in the Summary of the Invention section, uses a five term heat flow equation to account for sample and reference holder imbalances and differences in heating rate between the sample and reference holders. Heat flow results from that invention show improved dynamic response and hence improved resolution along with improvements in the empty DSC cell heat flow. However, the heat flow signal obtained from the practice of that invention still includes the effects of the sample pans.

The further calculation is a method for calculating sample heat flow in a differential scanning calorimeter that accounts for differences in heating rate between the sample and reference pans and the difference in heating rate between the sample and reference (if a reference is used). It may be applied to heat flux or power compensation DSCs, which are able to measure the sample and the reference heat flows independently and which account for imbalances and differences in heating rate between the sample and reference sections of the heat flow measuring apparatus.

Differential scanning calorimeters employing this method furnish a sample heat flow signal that is an accurate representation of the sample heat flow during the entire DSC experiment, free of the smearing effects that are present in conventional DSC. DSCs using this method will have greatly improved resolution. Kinetic analysis requiring partial integration of peak areas can be practiced using this method whereas conventional DSC cannot be used, due to the distortions of the sample heat flow signal.

This is a method for calculating sample heat flow, including the heat flow effects of the sample pans using heat flow signals obtained as described in the patent applications that are incorporated by reference herein. The result is a more accurate measurement of the sample heat flow during transitions when the heating rate of the sample differs from that of the reference. Resolution is improved because the return to baseline of the heat flow signal at the completion of a transformation is much more rapid.

Heat Flux DSCs

Figure 4:
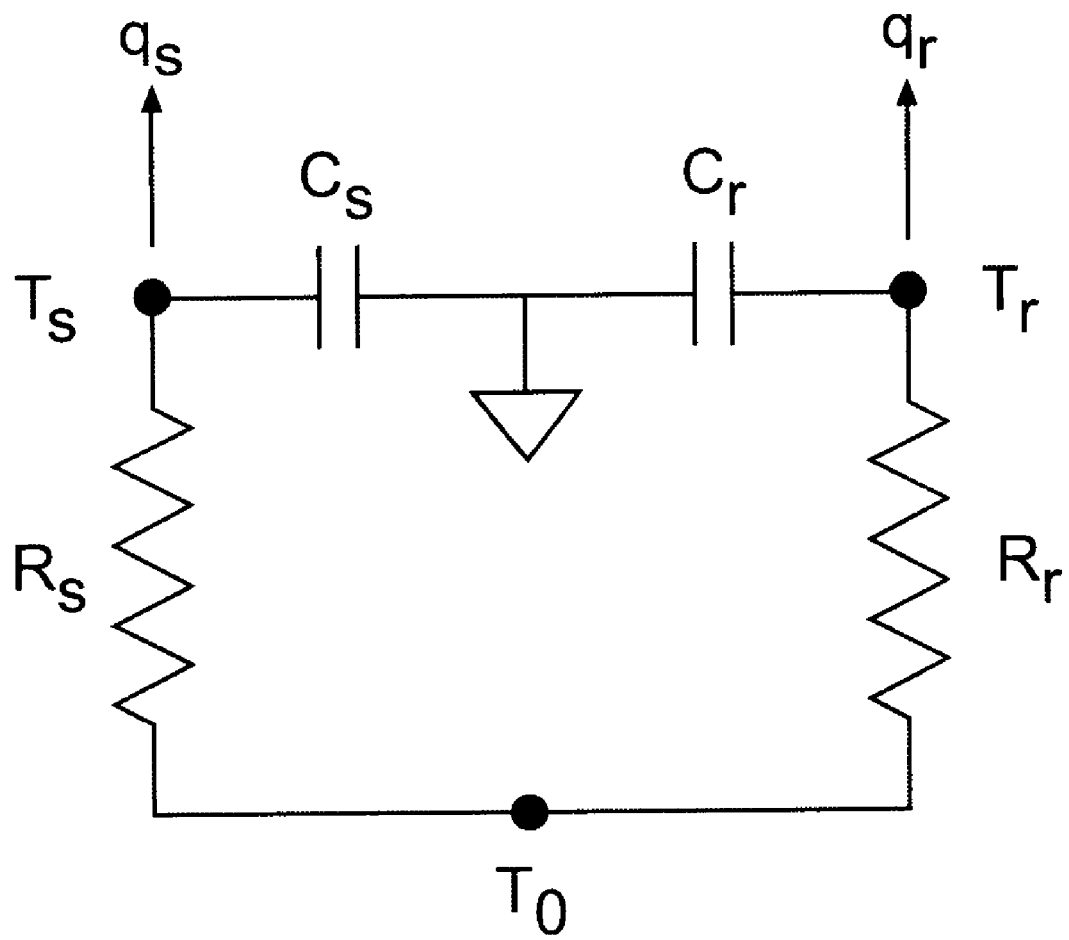
FIG. 4 is a thermal network model of a heat flux differential scanning calorimeter.

A heat flux DSC sensor according to the invention disclosed in the '949 application comprises independent sample and reference measuring sections that may be modeled using a thermal resistance and a thermal capacitance for each of the sample and reference sections as shown in FIG. 4. Thermal resistance and capacitance elements are idealizations of the sensor, which allow mathematical expressions describing the thermal behavior of the sensor to be written. $R_s$ and $R_r$ are thermal resistances, $C_s$ and $C_r$ are thermal capacitances representing the sample and reference sections of the sensor. $T_0$, $T_s$ and $T_r$ are the temperatures of the sensor base, sample position and reference positions. The heat flow to the sample and its pan and to the reference and its pan are $q_s$ and $q_r$, respectively.

Performing a heat balance on the sample and reference gives the heat flow differential equations.

$$q_s = \frac{T_0 - T_s}{R_s} - C_s \cdot \frac{dT_s}{d\tau} \quad q_r = \frac{T_0 - T_r}{R_r} - C_r \cdot \frac{dT_r}{d\tau}$$

In the preferred embodiment of the '949 invention, temperature $T_0$, the difference between the sensor base and sample position temperatures and the difference between the sample and reference position temperatures are measured. The differential temperatures are defined by.

$$\Delta T = T_s - T_r, \Delta T_0 = T_0 - T_s$$

Substituting into the heat balance equations gives, $$q_s = \frac{\Delta T_0}{R_s} - C_s \cdot \frac{dT_s}{d\tau} \text{ and } q_r = \frac{\Delta T_0 + \Delta T}{R_r} - C_r \cdot \left(\frac{dT_s}{d\tau} - \frac{d\Delta T}{d\tau}\right)$$

Sample temperature is obtained from the definition of $\Delta T_0$, $$T_s = T_0 - \Delta T_0$$

Thermal resistances and capacitances of the sensor as a function of temperature are obtained using the calibration method disclosed in the '949 application. Using thermal resistances and capacitances obtained by calibration with the temperatures and differential temperatures measured during a DSC experiment allows the sample and reference heat flows, $q_s$ and $q_r$ to be found. As used in the '949 invention and in conventional DSC, the difference between sample and reference heat flows is the desired result.

$$q = q_s - q_r$$

As noted above, the sample and reference heat flows include the heat flow to the sample and reference and to their pans.

$$q_s = q_{ss} + q_{ps} \quad q_r = q_{rs} + q_{pr}$$

Where, $q_{ss}$ is the sample heat flow, $q_{ps}$ is the sample pan heat flow, $q_{rs}$ is the reference heat flow and $q_{rp}$ is the reference pan heat flow. Because the pans and the reference do not have transitions, their heat flows are just the sensible heat associated with their specific heats:

$$q_{ps} = m_{ps} \cdot c_p \cdot \frac{dT_{ps}}{d\tau} \quad q_r = m_{pr} \cdot c_p \cdot \frac{dT_{pr}}{d\tau} + m_{rs} \cdot c_{rs} \cdot \frac{dT_{pr}}{d\tau}$$

Where, $m_{ps}$ and $m_{pr}$ are the masses of the sample and reference pans, $c_p$ is the specific heat of the pan material, $m_{rs}$ is the mass of the reference material, $c_{rs}$ is the specific heat of the reference material. The sample pan temperature is $T_{ps}$ and the reference pan temperature is $T_{pr}$. It is assumed that because the reference material has no transitions it heats at the same rate as the reference pan.

Substituting for the sample pan heat flow and solving for the sample heat flow:

$$q_{ss} = q_s - m_{ps} \cdot c_p \cdot \frac{dT_{ps}}{d\tau}$$

Solve the reference heat flow equation for the pan specific heat and substitute it into the sample heat flow equation.

$$q_{ss} = q_s - q_r \cdot \frac{m_{ps}}{m_{pr}} \cdot \frac{\frac{dT_{ps}}{d\tau}}{\frac{dT_{pr}}{d\tau}} + \frac{m_{ps}}{m_{pr}} \cdot m_{rs} \cdot c_{rs} \cdot \frac{dT_{ps}}{d\tau}$$

This equation gives the actual sample heat flow, accounting for the sample and reference pan heat flows and the heat flow to the reference. The second term on the right hand side is seen to be the reference heat flow multiplied by the ratio of the sample and reference pan masses and by the ratio of the sample and reference pan heating rates. It accounts for the fact that during a transition, the sample pan heats at a different rate than the reference pan because of the transition heat flow. The third term accounts for the heat flow to the reference material. In most cases, the reference pan is empty and the sample heat flow equation becomes.

$$q_{ss} = q_s - q_r \cdot \frac{m_{ps} \cdot \frac{dT_{ps}}{d\tau}}{m_{pr} \cdot \frac{dT_{pr}}{d\tau}}$$

When the sample heating rate is different from the reference heating rate, the fraction of reference heat flow subtracted from the sample heat flow is greater or less, depending upon whether the sample pan heating rate is greater or less than that of the reference pan. Because the reference heat flow is just the reference pan heat flow, this equation accounts for differences between sample and reference pan heating rates. For example, during a melt in DSC, the sample pan heating rate falls below the programmed rate, while the reference pan continues to heat at the programmed rate. In a conventional DSC the reference heat flow being subtracted from the sample heat flow is for a pan heating at the programmed rate. Thus, during the melt, too much heat is being subtracted from the sample heat flow and the heat flow signal is too small. During the baseline return, the sample pan is heating faster than the reference pan and insufficient heat flow is subtracted from the sample heat flow. As a consequence, the heat flow signal is too large.

To use the true sample heat flow equation requires that the sample and reference pan temperatures be known so that their derivatives may be taken. Unfortunately there is no way to measure the pan temperatures directly. The pan temperatures can be calculated using the temperature and heat flow signals.

The equations for heat flow from the sensor to the sample and reference pans are:

$$q_s = \frac{T_s - T_{ps}}{R_{ps}} \quad q_r = \frac{T_r - T_{pr}}{R_{pr}}$$

Solving for the pan temperatures.

$$T_{ps} = T_s - q_s \cdot R_{ps} \quad T_{pr} = T_r - q_r \cdot R_{pr}$$

Using these equations, pan temperatures and sample heat flows can be calculated from the measured signals. A predetermined function is used for the pan thermal resistances. Pan thermal resistance depends on the pan configuration, purge gas used in the DSC and the temperature of the DSC.

It must be noted that the present method cannot be applied to heat flux DSCs generally: the sample and the reference heat flows must be measured separately. The invention disclosed in the '949 application allows the sample and reference heat flows to be measured separately, and is required to apply use the present method.

Power Compensation DSCs

Figure 1:
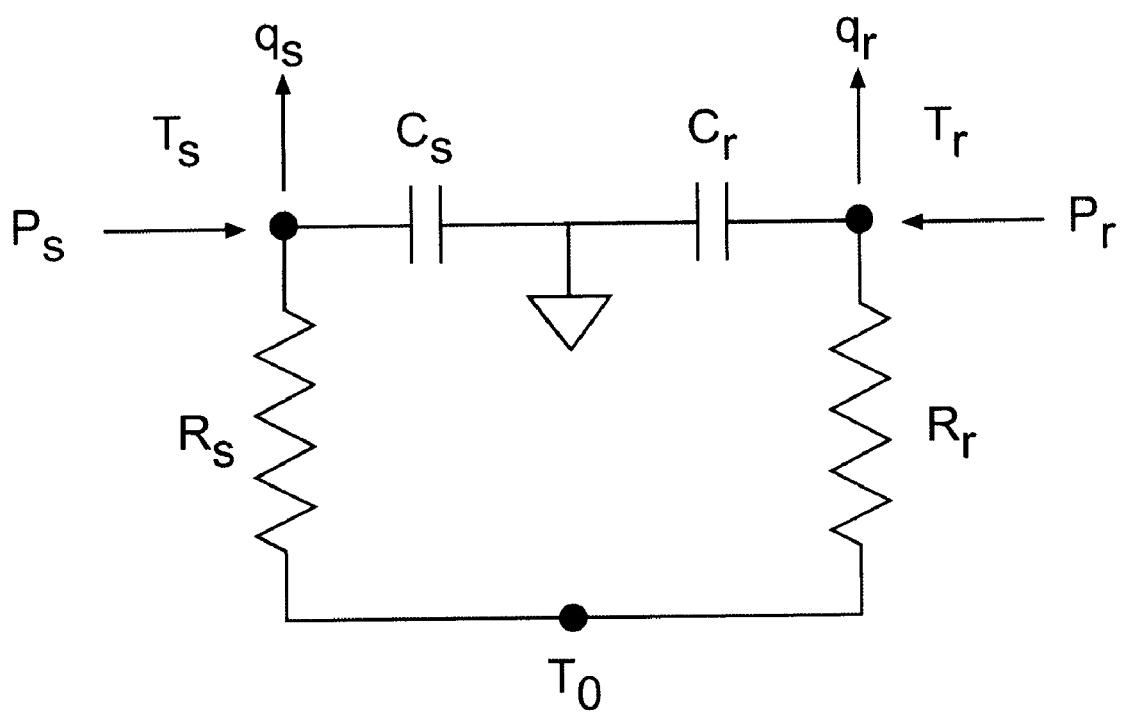
FIG. 1 is a thermal network model of an embodiment of the present invention.

A power compensation DSC that comprises independent sample and reference holders may be modeled using a thermal resistance and a thermal capacitance for each of the sample and reference holders as shown in FIG. 1. Thermal resistance and capacitance elements are idealizations of the sample and reference holders, which allow mathematical expressions describing the thermal behavior of the DSC to be written. $R_s$ and $R_r$ are thermal resistances, $C_s$ and $C_r$ are thermal capacitances representing the sample and reference holders. $T_0$, $T_s$ and $T_r$ are the temperatures of the isothermal enclosure, sample holder and reference holder. Heating power supplied to the sample holder is $p_s$, comprising the average heating power plus the differential power. Heating power supplied to the reference holder is $p_r$, comprising the average heating power minus the differential power. The heat flow to the sample and its pan and to the reference and its pan are $q_s$ and $q_r$.

Performing a heat balance on the sample and reference gives the heat flow differential equations, $$q_s = \frac{T_0 - T_s}{R_s} + p_s - C_s \cdot \frac{dT_s}{d\tau} \quad q_r = \frac{T_0 - T_r}{R_r} + p_r - C_r \cdot \frac{dT_r}{d\tau}$$

In the preferred embodiment of the '949 invention, temperature $T_0$, the difference between the isothermal enclosure and sample holder temperatures and the difference between the sample and reference holder temperatures are measured. The differential temperatures are defined by:

$$\Delta T = T_s - T_r, \ \Delta T_0 = T_0 - T_s$$

Substituting into the heat balance equations gives, $$q_s = \frac{\Delta T_0}{R_s} + p_s - C_s \cdot \frac{dT_s}{d\tau} \text{ and } q_r = \frac{\Delta T_0 + \Delta T}{R_r} + p_r - C_r \cdot \left(\frac{dT_s}{d\tau} - \frac{d\Delta T}{d\tau}\right)$$

Sample temperature is obtained from the definition of $\Delta T_0$, $$T_s = T_0 - \Delta T_0$$

Thermal resistances and capacitances of the sample and reference holders as a function of temperature are obtained using the calibration method disclosed in the '949 invention. Using thermal resistances and capacitances from calibration with the sample and reference holder power, temperatures and differential temperatures measured during a DSC experiment allows the sample and reference heat flow, $q_s$ and $q_r$ to be found. As used in the '949 invention and in conventional DSC, the difference between sample and reference heat flows is the desired result.

$$q = q_s - q_r$$

As noted above, the sample and reference heat flows include the heat flow to the sample and reference and to their pans.

$$q_s = q_{ss} + q_{ps} \quad q_r = q_{rs} + q_{pr}$$

Where $q_{ss}$ is the sample heat flow, $q_{ps}$ is the sample pan heat flow, $q_{rs}$ is the reference heat flow and $q_{rp}$ is the reference pan heat flow. The pans and the reference do not have transitions so that their heat flows are just the sensible heat associated with their specific heats:

$$q_{ps} = m_{ps} \cdot c_p \cdot \frac{dT_{ps}}{d\tau} \quad q_r = m_{pr} \cdot c_p \cdot \frac{dT_{pr}}{d\tau} + m_{rs} \cdot c_{rs} \cdot \frac{dT_{pr}}{d\tau}$$

Where $m_{ps}$ and $m_{pr}$ are the masses of the sample and reference pans, $c_p$ is the specific heat of the pan material, $m_{rs}$ is the mass of the reference material, $c_{rs}$ is the specific heat of the reference material. The sample pan temperature is $T_{ps}$ and the reference pan temperature is $T_{pr}$. It is assumed that because the reference material has no transitions it heats at the same rate as the reference pan.

Substituting for the sample pan heat flow and solving for the sample heat flow:

$$q_{ss} = q_s - m_{ps} \cdot c_p \cdot \frac{dT_{ps}}{d\tau}$$

Solving the reference heat flow equation for the pan specific heat and substituting it into the sample heat flow equation:

$$q_{ss} = q_s - q_r \cdot \frac{m_{ps}}{m_{pr}} \cdot \frac{\frac{dT_{ps}}{d\tau}}{\frac{dT_{pr}}{d\tau}} + \frac{m_{ps}}{m_{pr}} \cdot m_{rs} \cdot c_{rs} \cdot \frac{dT_{ps}}{d\tau}$$

This equation gives the actual sample heat flow, accounting for the sample and reference pan heat flows and the heat flow to the reference. The second term on the right hand side is seen to be the reference heat flow multiplied by the ratio of the sample and reference pan masses and by the ratio of the sample and reference pan heating rates. It accounts for the fact that during a transition, the sample pan heats at a different rate than the reference pan because of the transition heat flow. The third term accounts for the heat flow to the reference material. In most cases, the reference pan is empty and the sample heat flow equation becomes.

$$q_{ss} = q_s - q_r \cdot \frac{m_{ps} \cdot \frac{dT_{ps}}{d\tau}}{m_{pr} \cdot \frac{dT_{pr}}{d\tau}}$$

When the sample heating rate is different from the reference heating rate, the fraction of reference heat flow subtracted from the sample heat flow is greater or less, depending upon whether the sample pan heating rate is greater or less than that of the reference pan. Because the reference heat flow is just the reference pan heat flow, this equation accounts for differences between sample and reference pan heating rates. For example, during a melt in DSC, the sample pan heating rate falls below the programmed rate, while the reference pan continues to heat at the programmed rate. In a conventional DSC the reference heat flow being subtracted from the sample heat flow is for a pan heating at the programmed rate thus, during the melt too much heat is being subtracted from the sample heat flow and the heat flow signal is too small. During the baseline return, the sample pan is heating faster than the reference pan and insufficient heat flow is subtracted from the sample heat flow, consequently the heat flow signal is too large.

To use the true sample heat flow equation requires that the sample and reference pan temperatures be known so that their derivatives may be taken. Unfortunately there is no way to measure the pan temperatures directly. The pan temperatures can be calculated using the temperature and heat flow signals.

The equations for heat flow from the sample and reference holders to the sample and reference pans are:

$$q_s = \frac{T_s - T_{ps}}{R_{ps}} \quad q_r = \frac{T_r - T_{pr}}{R_{pr}}$$

Solving for the pan temperatures:

$$T_{ps} = T_s - q_s \cdot R_{ps} \quad T_{pr} = T_r - q_r \cdot R_{pr}$$

Using these equations, the pan temperatures and sample heat flows are obtained from measurements. A predetermined function is used for the pan thermal resistances. Pan thermal resistance depends on the pan configuration, purge gas used in the DSC and the temperature of the DSC.

It must be noted that the present method cannot be applied to power compensation DSCs generally. The sample and the reference heat flows must be measured separately. The invention disclosed in the power compensation continuation-in-part application to the '949 application referenced above allows the sample and reference heat flows to be measured separately and is required to practice the present method.

Experimental Results

Figure 5:
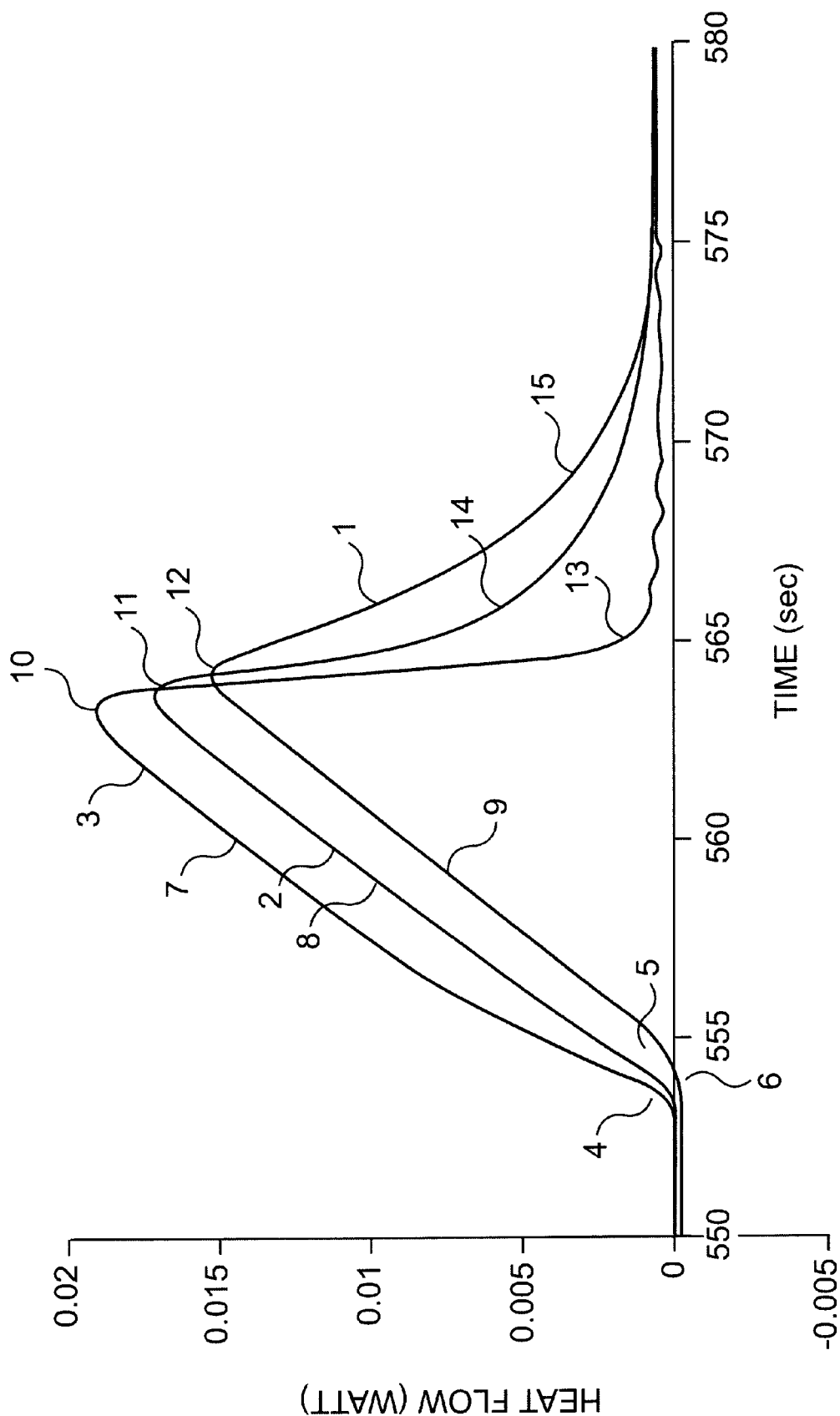
FIG. 5 is a plot showing a comparison of the heat flow obtained using the present method to the heat flow obtained using conventional DSCs, and to the heat flow obtained using the invention disclosed in the '949 application.

FIG. 5 shows the application of the improved calculation to the calculation of DSC heat flows in a heat flux DSC, for a 4.92 mg indium melt at 10° C./min plotted versus time. The conventional DSC result is the curve labeled 1, the result using the invention of the '949 application is labeled 2 and the result using the method of the improved calculation is labeled 3. Beginning at the left side of the plot, the onset of the indium melt for the improved calculation 4 occurs earlier and is steeper than the onset of indium that occurs using the invention of the '949 application 5, or using a conventional DSC 6. During the melt, the heat flow signal calculated using the improved calculation 7 is much larger than that obtained using the invention of the '949 application 8, which in turn is substantially larger than the signal obtained using conventional DSC 9. The melt is completed at the heat flow signal peak when the latent heat of fusion has been absorbed by the sample.

Also, the heat flow peak using the improved calculation 10 is higher and occurs slightly earlier compared to the peak of the '949 invention 11, and much higher and earlier still than the peak obtained using a conventional DSC 12. Immediately following the peak, the sample heat flow decreases rapidly as the flow of heat to the sample following the melt returns to the value just before the transition which, corresponds to the specific heat of the sample. The post melt decay of the heat flow signal 13 of the improved calculation is extremely rapid, while the post melt heat flow decay 14 of the '949 invention is much slower and the post melt decay 15 of conventional DSC is slower still. The complete indium melt heat flow signal 3 of the improved calculation comprising the onset 4, melt 7, peak heat flow 10 and post melt decay 13 is a much more accurate measurement than that of the '949 invention or of a conventional DSC.

The foregoing disclosure of embodiments of the present invention has been presented for purposes of illustration and description, it is not intended to be exhaustive or to limit the invention to the precise forms disclosed. Many variations and modifications of the embodiments described herein will be obvious to one of ordinary skill in the art in light of the above disclosure. The scope of the invention is to be defined only by the claims appended hereto, and by their equivalents.

What is claimed is:

1. A power compensation differential scanning calorimeter comprising:
    (a) an absolute temperature detector which measures one of a sample temperature, a reference temperature, and an isothermal enclosure temperature;
    (b) a first differential temperature detector which measures one of the difference between the sample temperature and the isothermal enclosure temperature, the difference between the reference temperature and the isothermal enclosure temperature, and the difference between the sample temperature and the reference temperature;
    (c) a second differential temperature detector which measures another one of the difference between the sample temperature and the reference temperature, the difference between the sample temperature and the isothermal enclosure temperature, and the difference between the reference temperature and the isothermal enclosure temperature; and
    (d) meters for measuring a differential power to the sample with respect to the reference,
    wherein the power compensation calorimeter is calibrated by running a first experiment with an empty cell according to a pre-selected temperature program, and running a second experiment, with a sample calibration specimen in a sample holder and a reference calibration specimen in a reference holder, according to the same pre-selected temperature program.

2. The power compensation differential scanning calorimeter of claim 1, further comprising means for calculating a sample thermal capacitance according to:

$$C_s = \frac{\Delta T_{o1} \cdot \left(m_{s2} \cdot C_{mat} \cdot \frac{dT_{s2}}{d\tau} - p_{s2}\right) + \Delta T_{o2} \cdot p_{s1}}{\Delta T_{o2} \cdot \frac{dT_{s1}}{d\tau} - \Delta T_{o1} \cdot \frac{dT_{s2}}{d\tau}}.$$

3. The power compensation differential scanning calorimeter of claim 1, further comprising means for calculating a sample thermal resistance according to:

$$R_s = \frac{\Delta T_{o2} \cdot \frac{dT_{s1}}{d\tau} - \Delta T_{o1} \cdot \frac{dT_{s2}}{d\tau}}{\frac{dT_{s1}}{d\tau} \cdot \left(m_{s2} \cdot C_{mat} \cdot \frac{dT_{s2}}{d\tau} - p_{s2}\right) + \frac{dT_{s2}}{d\tau} \cdot p_{s1}}.$$

4. The power compensation differential scanning calorimeter of claim 1, further comprising means for calculating a reference thermal capacitance according to:

$$C_r = \frac{(\Delta T_{o1} + \Delta T_1) \cdot \left[m_{r2} \cdot C_{mat} \cdot \left(\frac{dT_{s2}}{d\tau} - \frac{d\Delta T_2}{d\tau}\right) - p_{r2}\right] + (\Delta T_{o2} + \Delta T_2) \cdot p_{r1}}{(\Delta T_{o1} + \Delta T_1) \cdot \left(\frac{d\Delta T_2}{d\tau} - \frac{dT_{s2}}{d\tau}\right) + (\Delta T_{o2} + \Delta T_2) \cdot \left(\frac{dT_{s1}}{d\tau} - \frac{d\Delta T_1}{d\tau}\right)}.$$

5. The power compensation differential scanning calorimeter of claim 1, further comprising means for calculating a reference thermal resistance according to:

$$R_r = \frac{(\Delta T_{o1} + \Delta T_1) \cdot \left(\frac{d\Delta T_2}{d\tau} - \frac{dT_{s2}}{d\tau}\right) + (\Delta T_{o2} + \Delta T_2) \cdot \left(\frac{dT_{s1}}{d\tau} - \frac{d\Delta T_1}{d\tau}\right)}{\left[m_{r2} \cdot C_{mat} \cdot \left(\frac{dT_{s1}}{d\tau} - \frac{d\Delta T_1}{d\tau}\right) - p_{r2}\right] \cdot \left(\frac{dT_{s1}}{d\tau} - \frac{d\Delta T_1}{d\tau}\right) - p_{r1} \cdot \left(\frac{d\Delta T_2}{d\tau} - \frac{dT_{s2}}{d\tau}\right)}.$$

6. The power compensation differential scanning calorimeter of claim 1,
    wherein the absolute temperature detector measures the sample temperature, the first differential temperature detector measures the difference between the sample temperature and the isothermal enclosure temperature, and the second differential temperature detector measures the difference between the sample temperature and the reference temperature, and further comprising means for calculating a differential heat flow to the sample according to:

$$q = \Delta p + \Delta T_o \cdot \left(\frac{R_r - R_s}{R_r \cdot R_s}\right) - \frac{\Delta T}{R_r} + (C_r - C_s) \cdot \frac{dT_s}{d\tau} - C_r \cdot \frac{d\Delta T}{d\tau}.$$

7. A power compensation differential scanning calorimeter comprising:
   (a) an absolute temperature detector which measures one of a sample temperature, a reference temperature, and an isothermal enclosure temperature;
   (b) a first differential temperature detector which measures one of the difference between the sample temperature and the isothermal enclosure temperature, the difference between the reference temperature and the isothermal enclosure temperature, and the difference between the sample temperature and the reference temperature;
   (c) a second differential temperature detector which measures another one of the difference between the sample temperature and the reference temperature, the difference between the sample temperature and the isothermal enclosure temperature, and the difference between the reference temperature and the isothermal enclosure temperature; and
   (d) meters for measuring a differential power to the sample with respect to the reference,
      wherein the power compensation calorimeter is calibrated by running a first experiment with a first sample calibration specimen in a sample holder and a first reference calibration specimen in a reference holder according to a pre-selected temperature program, and running a second experiment, with a second sample calibration specimen in the sample holder and a second reference calibration specimen in the reference holder, according to the same pre-selected temperature program, wherein the first sample calibration specimen has a mass that is substantially different from the mass of the second sample calibration specimen.

8. The power compensation differential scanning calorimeter of claim 7, further comprising means for calculating a sample thermal capacitance according to:

$$C_s = \frac{\Delta T_{o1} \cdot \left(m_{s2} \cdot C_{mat} \cdot \frac{dT_{s2}}{d\tau} - p_{s2}\right) + \Delta T_{o2} \cdot \left(p_{s1} - m_{s1} \cdot C_{mat} \cdot \frac{dT_{s1}}{d\tau}\right)}{\Delta T_{o2} \cdot \frac{dT_{s1}}{d\tau} - \Delta T_{o1} \cdot \frac{dT_{s2}}{d\tau}}.$$

9. The power compensation differential scanning calorimeter of claim 7, further comprising means for calculating a sample thermal resistance according to:

$$R_s = \frac{\Delta T_{o2} \cdot \frac{dT_{s1}}{d\tau} - \Delta T_{o1} \cdot \frac{dT_{s2}}{d\tau}}{\frac{dT_{s1}}{d\tau} \cdot \left(m_{s2} \cdot C_{mat} \cdot \frac{dT_{s2}}{d\tau} - p_{s2}\right) + \frac{dT_{s2}}{d\tau} \cdot \left(p_{s1} - m_{s1} \cdot C_{mat} \cdot \frac{dT_{s1}}{d\tau}\right)}.$$

10. The power compensation differential scanning calorimeter of claim 7, further comprising means for calculating a reference thermal capacitance according to:

$$C_r = \frac{(\Delta T_{o1} + \Delta T_1) \cdot \left[m_{r2} \cdot C_{mat} \cdot \left(\frac{dT_{s2}}{d\tau} - \frac{d\Delta T_2}{d\tau}\right) - p_{r2}\right] +}{(\Delta T_{o1} + \Delta T_1) \cdot \left(\frac{d\Delta T_2}{d\tau} - \frac{dT_{s2}}{d\tau}\right) +} \\ \frac{(\Delta T_{o2} + \Delta T_2) \cdot \left[p_{r1} - m_{r1} \cdot C_{mat} \cdot \left(\frac{dT_{s1}}{d\tau} - \frac{d\Delta T_1}{d\tau}\right)\right]}{(\Delta T_{o2} + \Delta T_2) \cdot \left(\frac{dT_{s1}}{d\tau} - \frac{d\Delta T_1}{d\tau}\right)}.$$

11. The power compensation differential scanning calorimeter of claim 7, further comprising means for calculating a reference thermal resistance according to:

$$R_r = \frac{(\Delta T_{o1} + \Delta T_1) \cdot \left(\frac{d\Delta T_2}{d\tau} - \frac{dT_{s2}}{d\tau}\right) +}{\left(\frac{dT_{s1}}{d\tau} - \frac{d\Delta T_1}{d\tau}\right) \cdot \left[m_{r2} \cdot C_{mat} \cdot \left(\frac{dT_{s2}}{d\tau} - \frac{d\Delta T_2}{d\tau}\right) - p_{r2}\right] +} \\ \frac{(\Delta T_{o2} + \Delta T_2) \cdot \left(\frac{dT_{s1}}{d\tau} - \frac{d\Delta T_1}{d\tau}\right)}{\left(\frac{dT_{s2}}{d\tau} - \frac{d\Delta T_2}{d\tau}\right) \cdot \left[p_{r1} - m_{r1} \cdot C_{mat} \cdot \left(\frac{dT_{s1}}{d\tau} - \frac{d\Delta T_1}{d\tau}\right)\right]}.$$

12. The power compensation differential scanning calorimeter of claim 7,
   wherein the absolute temperature detector measures the sample temperature, the first differential temperature detector measures the difference between the sample temperature and the isothermal enclosure temperature, and the second differential temperature detector measures the difference between the sample temperature and the reference temperature, and
   further comprising means for calculating a differential heat flow to the sample according to:

$$q = \Delta p + \Delta T_o \cdot \left(\frac{R_r - R_s}{R_r \cdot R_s}\right) - \frac{\Delta T}{R_r} + (C_r - C_s) \cdot \frac{dT_s}{d\tau} - C_r \cdot \frac{d\Delta T}{d\tau}.$$

13. A method for determining differential heat flow to a sample with respect to a reference in a power compensation differential scanning calorimeter comprising:
   (a) calibrating the calorimeter by measuring a sample thermal resistance, a sample thermal capacitance, a reference thermal resistance and a reference thermal capacitance; and
   (b) using a five-term heat flow equation to determine the differential heat flow to the sample with respect to the reference.

14. The method of claim 13, wherein the step of measuring the sample thermal resistance comprises using the equation:

$$R_s = \frac{\Delta T_{o2} \cdot \frac{dT_{s1}}{d\tau} - \Delta T_{o1} \cdot \frac{dT_{s2}}{d\tau}}{\frac{dT_{s1}}{d\tau} \cdot \left(m_{s2} \cdot C_{mat} \cdot \frac{dT_{s2}}{d\tau} - p_{s2}\right) + \frac{dT_{s2}}{d\tau} \cdot p_{s1}}.$$

15. The method of claim 13, wherein the step of measuring the sample thermal capacitance comprises using the equation:

$$C_s = \frac{\Delta T_{o1} \cdot \left(m_{s2} \cdot C_{mat} \cdot \frac{dT_{s2}}{d\tau} - p_{s2}\right) + \Delta T_{o2} \cdot p_{s1}}{\Delta T_{o2} \cdot \frac{dT_{s1}}{d\tau} - \Delta T_{o1} \cdot \frac{dT_{s2}}{d\tau}}.$$

16. The method of claim 13, wherein the step of measuring the reference thermal resistance comprises using the equation:

$$R_r = \frac{(\Delta T_{o1} + \Delta T_1) \cdot \left(\frac{d\Delta T_2}{d\tau} - \frac{dT_{s2}}{d\tau}\right) + (\Delta T_{o2} + \Delta T_2) \cdot \left(\frac{dT_{s1}}{d\tau} - \frac{d\Delta T_1}{d\tau}\right)}{\left[m_{r2} \cdot C_{mat} \cdot \left(\frac{dT_{s1}}{d\tau} - \frac{d\Delta T_1}{d\tau}\right) - p_{r2}\right] \cdot \left(\frac{dT_{s1}}{d\tau} - \frac{d\Delta T_1}{d\tau}\right) - p_{r1} \cdot \left(\frac{d\Delta T_2}{d\tau} - \frac{dT_{s2}}{d\tau}\right)}.$$

17. The method of claim 13, wherein the step of measuring the reference thermal capacitance comprises using the equation:

$$C_r = \frac{(\Delta T_{o1} + \Delta T_1) \cdot \left[m_{r2} \cdot C_{mat} \cdot \left(\frac{dT_{s2}}{d\tau} - \frac{d\Delta T_2}{d\tau}\right) - p_{r2}\right] + (\Delta T_{o2} + \Delta T_2) \cdot p_{r1}}{(\Delta T_{o1} + \Delta T_1) \cdot \left(\frac{d\Delta T_2}{d\tau} - \frac{dT_{s2}}{d\tau}\right) + (\Delta T_{o2} + \Delta T_2) \cdot \left(\frac{dT_{s1}}{d\tau} - \frac{d\Delta T_1}{d\tau}\right)}.$$

18. The method of claim 13, wherein the step of measuring the sample thermal resistance comprises using the equation:

$$R_s = \frac{\Delta T_{o2} \cdot \frac{dT_{s1}}{d\tau} - \Delta T_{o1} \cdot \frac{dT_{s2}}{d\tau}}{\frac{dT_{s1}}{d\tau} \cdot \left(m_{s2} \cdot C_{mat} \cdot \frac{dT_{s2}}{d\tau} - p_{s2}\right) + \frac{dT_{s2}}{d\tau} \cdot \left(p_{s1} - m_{s1} \cdot C_{mat} \cdot \frac{dT_{s1}}{d\tau}\right)}.$$

19. The method of claim 13, wherein the step of measuring the sample thermal capacitance comprises using the equation:

$$C_s = \frac{\Delta T_{o1} \cdot \left(m_{s2} \cdot C_{mat} \cdot \frac{dT_{s2}}{d\tau} - p_{s2}\right) + \Delta T_{o2} \cdot \left(p_{s1} - m_{s1} \cdot C_{mat} \cdot \frac{dT_{s1}}{d\tau}\right)}{\Delta T_{o2} \cdot \frac{dT_{s1}}{d\tau} - \Delta T_{o1} \cdot \frac{dT_{s2}}{d\tau}}.$$

20. The method of claim 13, wherein the step of measuring the reference thermal resistance comprises using the equation:

$$R_r = \frac{(\Delta T_{o1} + \Delta T_1) \cdot \left(\frac{d\Delta T_2}{d\tau} - \frac{dT_{s2}}{d\tau}\right) + (\Delta T_{o2} + \Delta T_2) \cdot \left(\frac{dT_{s1}}{d\tau} - \frac{d\Delta T_1}{d\tau}\right)}{\left(\frac{dT_{s1}}{d\tau} - \frac{d\Delta T_1}{d\tau}\right) \cdot \left[m_{r2} \cdot C_{mat} \cdot \left(\frac{dT_{s2}}{d\tau} - \frac{d\Delta T_2}{d\tau}\right) - p_{r2}\right] + \left(\frac{dT_{s2}}{d\tau} - \frac{d\Delta T_2}{d\tau}\right) \cdot \left[p_{r1} - m_{r1} \cdot C_{mat} \cdot \left(\frac{dT_{s1}}{d\tau} - \frac{d\Delta T_1}{d\tau}\right)\right]}.$$

21. The method of claim 13, wherein the step of measuring the reference thermal capacitance comprises using the equation:

$$C_r = \frac{(\Delta T_{o1} + \Delta T_1) \cdot \left[m_{r2} \cdot C_{mat} \cdot \left(\frac{dT_{s2}}{d\tau} - \frac{d\Delta T_2}{d\tau}\right) - p_{r2}\right] + (\Delta T_{o2} + \Delta T_2) \cdot \left[p_{r1} - m_{r1} \cdot C_{mat} \cdot \left(\frac{dT_{s1}}{d\tau} - \frac{d\Delta T_1}{d\tau}\right)\right]}{(\Delta T_{o1} + \Delta T_1) \cdot \left(\frac{d\Delta T_2}{d\tau} - \frac{dT_{s2}}{d\tau}\right) + (\Delta T_{o2} + \Delta T_2) \cdot \left(\frac{dT_{s1}}{d\tau} - \frac{d\Delta T_1}{d\tau}\right)}.$$

22. The method of claim 13, comprising storing the sample thermal resistance, sample thermal capacitance, reference thermal resistance, and reference thermal capacitance as tabular data.

23. The method of claim 13, comprising fitting the sample thermal resistance, sample thermal capacitance, reference thermal resistance, and reference thermal capacitance to a mathematical expression.

24. The method of claim 23, wherein the mathematical expression is a polynomial.

25. A method for determining differential heat flow to a sample with respect to a reference using a power compensation differential scanning calorimeter comprising:

(a) calibrating the power compensation differential scanning calorimeter by measuring a sample thermal resistance, a sample thermal capacitance, a reference thermal resistance, and a reference thermal capacitance over a first range of temperatures;

(b) placing a sample on a sample holder in the power compensation differential scanning calorimeter;

(c) increasing the temperature of the sample over a second range of temperatures, wherein the second range of temperatures does not exceed the first range of temperatures;

(d) measuring differential power to the sample with respect to the reference, differential temperature between the sample holder and a reference holder, differential temperature between the sample holder and an isothermal enclosure, and a sample temperature; and (e) determining the differential heat flow to the sample with respect to the reference using a five-term heat flow equation as follows:

$$q = \Delta p + \Delta T_o \cdot \left(\frac{R_r - R_s}{R_r \cdot R_s}\right) - \frac{\Delta T}{R_r} + (C_r - C_s) \cdot \frac{dT_s}{d\tau} - C_r \cdot \frac{d\Delta T}{d\tau}$$

at temperatures within the second range of temperatures.

26. The power compensation differential scanning calorimeter method of claim 25, wherein the step of measuring the sample thermal capacitance comprises using the equation:

$$C_s = \frac{\Delta T_{o1} \cdot \left(m_{s2} \cdot C_{mat} \cdot \frac{dT_{s2}}{d\tau} - p_{s2}\right) + \Delta T_{o2} \cdot p_{s1}}{\Delta T_{o2} \cdot \frac{dT_{s1}}{d\tau} - \Delta T_{o1} \cdot \frac{dT_{s2}}{d\tau}}.$$

27. The power compensation differential scanning calorimeter method of claim 25, wherein the step of measuring the sample thermal resistance comprises using the equation:

$$R_s = \frac{\Delta T_{o2} \cdot \frac{dT_{s1}}{d\tau} - \Delta T_{o1} \cdot \frac{dT_{s2}}{d\tau}}{\frac{dT_{s1}}{d\tau} \cdot \left(m_{s2} \cdot C_{mat} \cdot \frac{dT_{s2}}{d\tau} - p_{s2}\right) + \frac{dT_{s2}}{d\tau} \cdot p_{s1}}.$$

28. The power compensation differential scanning calorimeter method of claim 25, wherein the step of measuring the reference thermal capacitance comprises using the equation:

$$C_r = \frac{(\Delta T_{o1} + \Delta T_1) \cdot \left[m_{r2} \cdot C_{mat} \cdot \left(\frac{dT_{s2}}{d\tau} - \frac{d\Delta T_2}{d\tau}\right) - p_{r2}\right] + (\Delta T_{o2} + \Delta T_2) \cdot p_{r1}}{(\Delta T_{o1} + \Delta T_1) \cdot \left(\frac{d\Delta T_2}{d\tau} - \frac{dT_{s2}}{d\tau}\right) + (\Delta T_{o2} + \Delta T_2) \cdot \left(\frac{dT_{s1}}{d\tau} - \frac{d\Delta T_1}{d\tau}\right)}.$$

29. The power compensation differential scanning calorimeter method of claim 25, wherein the step of measuring the reference thermal resistance comprises using the equation:

$$R_r = \frac{(\Delta T_{o1} + \Delta T_1) \cdot \left(\frac{d\Delta T_2}{d\tau} - \frac{dT_{s2}}{d\tau}\right) + (\Delta T_{o2} + \Delta T_2) \cdot \left(\frac{dT_{s1}}{d\tau} - \frac{d\Delta T_1}{d\tau}\right)}{\left[m_{r2} \cdot C_{mat} \cdot \left(\frac{dT_{s1}}{d\tau} - \frac{d\Delta T_1}{d\tau}\right) - p_{r2}\right] \cdot \left(\frac{dT_{s1}}{d\tau} - \frac{d\Delta T_1}{d\tau}\right) - p_{r1} \cdot \left(\frac{d\Delta T_2}{d\tau} - \frac{dT_{s2}}{d\tau}\right)}.$$

30. The method of claim 25, wherein the step of measuring the sample thermal resistance comprises using the equation:

$$R_s = \frac{\Delta T_{o2} \cdot \frac{dT_{s1}}{d\tau} - \Delta T_{o1} \cdot \frac{dT_{s2}}{d\tau}}{\frac{dT_{s1}}{d\tau} \cdot \left(m_{s2} \cdot C_{mat} \cdot \frac{dT_{s2}}{d\tau} - p_{s2}\right) + \frac{dT_{s2}}{d\tau} \cdot \left(p_{s1} - m_{s1} \cdot C_{mat} \cdot \frac{dT_{s1}}{d\tau}\right)}.$$

31. The method of claim 25, wherein the step of measuring the sample thermal capacitance comprises using the equation:

$$C_s = \frac{\Delta T_{o1} \cdot \left(m_{s2} \cdot C_{mat} \cdot \frac{dT_{s2}}{d\tau} - p_{s2}\right) + \Delta T_{o2} \cdot \left(p_{s1} - m_{s1} \cdot C_{mat} \cdot \frac{dT_{s1}}{d\tau}\right)}{\Delta T_{o2} \cdot \frac{dT_{s1}}{d\tau} - \Delta T_{o1} \cdot \frac{dT_{s2}}{d\tau}}.$$

32. The method of claim 25, wherein the step of measuring the reference thermal resistance comprises using the equation:

$$R_r = \frac{(\Delta T_{o1} + \Delta T_1) \cdot \left(\frac{d\Delta T_2}{d\tau} - \frac{dT_{s2}}{d\tau}\right) + (\Delta T_{o2} + \Delta T_2) \cdot \left(\frac{dT_{s1}}{d\tau} - \frac{d\Delta T_1}{d\tau}\right)}{\left(\frac{dT_{s1}}{d\tau} - \frac{d\Delta T_1}{d\tau}\right) \cdot \left[m_{r2} \cdot C_{mat} \cdot \left(\frac{dT_{s2}}{d\tau} - \frac{d\Delta T_2}{d\tau}\right) - p_{r2}\right] + \left(\frac{dT_{s2}}{d\tau} - \frac{d\Delta T_2}{d\tau}\right) \cdot \left[p_{r1} - m_{r1} \cdot C_{mat} \cdot \left(\frac{dT_{s1}}{d\tau} - \frac{d\Delta T_1}{d\tau}\right)\right]}.$$

33. The method of claim 25, wherein the step of measuring the reference thermal capacitance comprises using the equation:

$$C_r = \frac{(\Delta T_{o1} + \Delta T_1) \cdot \left[m_{r2} \cdot C_{mat} \cdot \left(\frac{dT_{s2}}{d\tau} - \frac{d\Delta T_2}{d\tau}\right) - p_{r2}\right] + (\Delta T_{o2} + \Delta T_2) \cdot \left[p_{r1} - m_{r1} \cdot C_{mat} \cdot \left(\frac{dT_{s1}}{d\tau} - \frac{d\Delta T_1}{d\tau}\right)\right]}{(\Delta T_{o1} + \Delta T_1) \cdot \left(\frac{d\Delta T_2}{d\tau} - \frac{dT_{s2}}{d\tau}\right) + (\Delta T_{o2} + \Delta T_2) \cdot \left(\frac{dT_{s1}}{d\tau} - \frac{d\Delta T_1}{d\tau}\right)}.$$

34. The method of claim 25, comprising storing the sample thermal resistance, sample thermal capacitance, reference thermal resistance, and reference thermal capacitance as tabular data.

35. The method of claim 25, comprising fitting the sample thermal resistance, sample thermal capacitance, reference thermal resistance, and reference thermal capacitance to a mathematical expression.

36. The method of claim 35, wherein the mathematical expression is a polynomial.

37. A method for measuring the differential heat flow to a sample with respect to a reference using a power compensation differential scanning calorimeter comprising:
(a) calibrating the calorimeter by measuring a sample thermal resistance, a sample thermal capacitance, a reference thermal resistance, and a reference thermal capacitance;
(b) measuring individually a power supplied to a sample holder, a power supplied to a reference holder, an isothermal enclosure temperature, a sample holder temperature, and a reference holder temperature; and
(c) calculating the differential heat flow to the sample with respect to the reference using a six-term equation as follows:

$$q = p_s - p_r + \frac{T_o - T_s}{R_s} - \frac{T_o - T_r}{R_r} - C_s \cdot \frac{dT_s}{d\tau} + C_r \cdot \frac{dT_r}{d\tau}.$$

38. A power compensation differential scanning calorimeter comprising:
(a) an isothermal enclosure;
(b) a sample holder installed in the isothermal enclosure and supported by a sample thermal resistor having a small cross-sectional area in the direction normal to the heat flow to the sample holder, wherein the sample holder has a sample temperature detector and a sample heating element, and is adapted to receive a sample;
(c) a reference holder installed in the isothermal enclosure and supported by a reference thermal resistor having a small cross-sectional area in the direction normal to the heat flow to the reference holder, wherein the reference holder has a reference temperature detector and a reference heating element, and is adapted to at receive a reference; and
(d) an isothermal enclosure temperature detector for measuring the isothermal temperature.

39. The power compensation differential scanning calorimeter of claim 38, wherein the sample temperature detector measures absolute temperature.

40. The power compensation differential scanning calorimeter of claim 38, wherein the power compensation differential scanning calorimeter measures a first differential temperature between the sample holder and the reference holder, a second differential temperature between the sample holder and the isothermal enclosure, and a differential power between the sample and the reference.

41. The power compensation differential scanning calorimeter of claim 40, wherein the differential power between the sample and the reference is measured by separately measuring power to the sample holder and power to the reference holder, and calculating a difference between the power to the sample holder and the power to the reference holder.

42. The power compensation differential scanning calorimeter of claim 41, wherein the power to the sample holder and the power to the reference holder are measured by instrumentation that measures voltages and currents to the sample heating element and the reference heating element.

43. The power compensation differential scanning calorimeter of claim 38, wherein the isothermal enclosure is cooled and is constructed of a high conductivity material.

44. The power compensation differential scanning calorimeter of claim 38, wherein the sample holder contains a sample pan for receiving the sample, and wherein the sample holder has a lid for enclosing the sample inside the sample holder.

45. The power compensation differential scanning calorimeter of claim 38, wherein the reference holder contains a reference pan for receiving the reference, and wherein the reference holder has a lid for enclosing the reference inside the reference holder.

46. The power compensation differential scanning calorimeter of claim 38, wherein the sample thermal resistor is a principal path for heat exchange between the sample holder and the isothermal enclosure, and the reference thermal resistor is a principal path for heat exchange between the reference holder and the isothermal enclosure.

47. The power compensation differential scanning calorimeter of claim 38, wherein the differential heat flow to the sample with respect to the reference is calculated using a five-term heat flow equation.

48. A method for calibrating a power compensation differential scanning calorimeter having an isothermal enclosure containing a sample holder holding a sample and a reference holder holding a reference, the method comprising the steps of:
   (a) running a first experiment with the differential scanning calorimeter empty, using a thermal program comprising a first isothermal segment, a second constant heating rate segment, and a third isothermal segment;
   (b) running a second experiment with specimens loaded in the sample holder and the reference holder, using the thermal program of the first experiment; and
   (c) calculating a sample thermal capacitance, a reference thermal capacitance, a sample thermal resistance, and a reference thermal resistances,
      wherein the differential scanning calorimeter is calibrated by calculating the sample thermal capacitance, the reference thermal capacitance, the sample thermal resistance, and the reference thermal resistance.

49. The method of claim 48, wherein each of the steps of running the first experiment and running the second experiment further comprise:
   (i) measuring one of a sample temperature, a reference temperature, and an isothermal enclosure temperature;
   (ii) measuring one of a difference between a sample temperature and an isothermal enclosure temperature, a difference between the reference temperature and the isothermal enclosure temperature, and a difference between the sample temperature and the reference temperature;
   (iii) measuring another one of the difference between the sample temperature and the reference temperature, the difference between the sample temperature and the isothermal enclosure temperature, and the difference between the reference temperature and the isothermal enclosure temperature; and
   (iv) measuring a differential power to a sample with respect to a reference.

50. The method of claim 48, wherein the first isothermal segment temperature is less than the lowest temperature in a desired temperature calibration range, and the third isothermal segment temperature is greater than the highest temperature in the desired temperature calibration range.

51. The method of claim 48, wherein the sample thermal capacitance is calculated according to:

$$C_s = \frac{\Delta T_{o1} \cdot \left(m_{s2} \cdot C_{mat} \cdot \frac{dT_{s2}}{d\tau} - p_{s2}\right) + \Delta T_{o2} \cdot p_{s1}}{\Delta T_{o2} \cdot \frac{dT_{s1}}{d\tau} - \Delta T_{o1} \cdot \frac{dT_{s2}}{d\tau}}.$$

52. The method of claim 48, wherein the sample thermal resistance is calculated according to:

$$R_s = \frac{\Delta T_{o2} \cdot \frac{dT_{s1}}{d\tau} - \Delta T_{o1} \cdot \frac{dT_{s2}}{d\tau}}{\frac{dT_{s1}}{d\tau} \cdot \left(m_{s2} \cdot C_{mat} \cdot \frac{dT_{s2}}{d\tau} - p_{s2}\right) + \frac{dT_{s2}}{d\tau} \cdot p_{s1}}.$$

53. The method of claim 48, wherein the reference thermal capacitance is calculated according to:

$$C_r = \frac{(\Delta T_{o1} + \Delta T_1) \cdot \left[m_{r2} \cdot C_{mat}\left(\frac{dT_{s2}}{d\tau} - \frac{d\Delta T_2}{d\tau}\right) - p_{r2}\right] + (\Delta T_{o2} + \Delta T_2) \cdot p_{r1}}{(\Delta T_{o1} + \Delta T_1) \cdot \left(\frac{d\Delta T_2}{d\tau} - \frac{dT_{s2}}{d\tau}\right) + (\Delta T_{o2} + \Delta T_2) \cdot \left(\frac{dT_{s1}}{d\tau} - \frac{d\Delta T_1}{d\tau}\right)}.$$

54. The method of claim 48, wherein the reference thermal resistance is calculated according to:

$$R_r = \frac{(\Delta T_{o1} + \Delta T_1) \cdot \left(\frac{d\Delta T_2}{d\tau} - \frac{dT_{s2}}{d\tau}\right) + (\Delta T_{o2} + \Delta T_2) \cdot \left(\frac{dT_{s1}}{d\tau} - \frac{d\Delta T_1}{d\tau}\right)}{\left[m_{r2} \cdot C_{mat} \cdot \left(\frac{dT_{s1}}{d\tau} - \frac{d\Delta T_1}{d\tau}\right) - p_{r2}\right] \cdot \left(\frac{dT_{s1}}{d\tau} - \frac{d\Delta T_1}{d\tau}\right) - p_{r1} \cdot \left(\frac{d\Delta T_2}{d\tau} - \frac{dT_{s2}}{d\tau}\right)}.$$

55. A method for calibrating a power compensation differential scanning calorimeter having an isothermal enclosure containing a sample holder holding a sample and a reference holder holding a reference, the method comprising the steps of:
   (a) running a first experiment with a first sample specimen in the sample holder and a first reference specimen in the reference holder, using a thermal program comprising a first isothermal segment, a second constant heating rate segment, and a third isothermal segment;
   (b) running a second experiment with a second sample specimen in the sample holder and a second reference sample in the reference holder, using the thermal program of the first experiment; and
   (c) calculating a sample thermal capacitance, a reference thermal capacitance, a sample thermal resistance, and a reference thermal resistance.

56. The method of claim 55, wherein the first sample specimen has a mass substantially different than the second sample specimen.

57. The method of claim 55, wherein the first sample specimen, the first reference specimen, the second sample specimen, and the second reference specimen are sapphire specimens.

58. The method of claim 57, wherein the sapphire specimens have masses ranging from 25 to 75 mg.

59. The method of claim 55, wherein sample thermal capacitance is calculated according to:

$$C_s = \frac{\Delta T_{o1} \cdot \left(m_{s2} \cdot C_{mat} \cdot \frac{dT_{s2}}{d\tau} - p_{s2}\right) + \Delta T_{o2} \cdot \left(p_{s1} - m_{s1} \cdot C_{mat} \cdot \frac{dT_{s1}}{d\tau}\right)}{\Delta T_{o2} \cdot \frac{dT_{s1}}{d\tau} - \Delta T_{o1} \cdot \frac{dT_{s2}}{d\tau}}.$$

60. The method of claim 55, wherein sample thermal resistance is calculated according to:

$$R_s = \frac{\Delta T_{o2} \cdot \frac{dT_{s1}}{d\tau} - \Delta T_{o1} \cdot \frac{dT_{s2}}{d\tau}}{\frac{dT_{s1}}{d\tau} \cdot \left(m_{s2} \cdot C_{mat} \cdot \frac{dT_{s2}}{d\tau} - p_{s2}\right) + \frac{dT_{s2}}{d\tau} \cdot \left(p_{s1} - m_{s1} \cdot C_{mat} \cdot \frac{dT_{s1}}{d\tau}\right)}.$$

61. The method of claim 55, wherein reference thermal capacitance is calculated according to:

$$C_r = \frac{(\Delta T_{o1} + \Delta T_1) \cdot \left[m_{r2} \cdot C_{mat} \cdot \left(\frac{dT_{s2}}{d\tau} - \frac{d\Delta T_2}{d\tau}\right) - p_{r2}\right] +}{(\Delta T_{o1} + \Delta T_1) \cdot \left(\frac{d\Delta T_2}{d\tau} - \frac{dT_{s2}}{d\tau}\right) +} \\ \frac{(\Delta T_{o2} + \Delta T_2) \cdot \left[p_{r1} - m_{r1} \cdot C_{mat} \cdot \left(\frac{dT_{s1}}{d\tau} - \frac{d\Delta T_1}{d\tau}\right)\right]}{(\Delta T_{o2} + \Delta T_2) \cdot \left(\frac{dT_{s1}}{d\tau} - \frac{d\Delta T_1}{d\tau}\right)}.$$

62. The method of claim 55, wherein reference thermal resistance is calculated according to:

$$R_r = \frac{(\Delta T_{o1} + \Delta T_1) \cdot \left(\frac{d\Delta T_2}{d\tau} - \frac{dT_{s2}}{d\tau}\right) + (\Delta T_{o2} + \Delta T_2) \cdot \left(\frac{dT_{s1}}{d\tau} - \frac{d\Delta T_1}{d\tau}\right)}{\left(\frac{dT_{s1}}{d\tau} - \frac{d\Delta T_1}{d\tau}\right) \cdot \left[m_{r2} \cdot C_{mat} \cdot \left(\frac{dT_{s2}}{d\tau} - \frac{d\Delta T_2}{d\tau}\right) - p_{r2}\right] + \left(\frac{dT_{s2}}{d\tau} - \frac{d\Delta T_2}{d\tau}\right) \cdot \left[p_{r1} - m_{r1} \cdot C_{mat} \cdot \left(\frac{dT_{s1}}{d\tau} - \frac{d\Delta T_1}{d\tau}\right)\right]}.$$

63. A power compensation differential scanning calorimeter comprising:

(a) an isothermal enclosure;

(b) a sample holder contained in the isothermal enclosure, the sample holder holding a sample;

(c) a reference holder contained in the isothermal enclosure, the reference holder holding a reference;

(d) temperature detectors for measuring an isothermal enclosure temperature, a sample holder temperature, and a reference holder temperature; and (e) power meters for measuring individually a power supplied to the sample holder and a power supplied to the reference holder, wherein differential heat flow to the sample with respect to the reference is calculated using a six-term equation as follows:

$$q = p_s - p_r + \frac{T_o - T_s}{R_s} - \frac{T_o - T_r}{R_r} - C_s \cdot \frac{dT_s}{d\tau} + C_r \cdot \frac{dT_r}{d\tau}.$$

64. The power compensation differential scanning calorimeter of claim 63, wherein the power compensation differential scanning calorimeter is calibrated by measuring a sample thermal resistance, a sample thermal capacitance, a reference thermal resistance, and a reference thermal capacitance.

65. The power compensation differential scanning calorimeter of claim 63, wherein the power compensation differential scanning calorimeter is calibrated by running a first experiment with an empty cell according to a pre-selected temperature program, and running a second experiment, with a sample specimen in the sample holder and a reference specimen in the reference holder, according to the pre-selected temperature program.

66. The power compensation differential scanning calorimeter of claim 63, wherein the power compensation differential scanning calorimeter is calibrated by running a first experiment with a first sample specimen in the sample holder and a first reference specimen in the reference holder according to a pre-selected temperature program, and running a second experiment, with a second sample specimen in the sample holder and a second reference specimen in the reference holder, according to the pre-selected temperature program, wherein the first sample specimen has a mass that is substantially different from a mass of the second sample specimen.

* * * * *